(12) United States Patent
Slotman

(10) Patent No.: US 7,297,546 B2
(45) Date of Patent: *Nov. 20, 2007

(54) METHODS FOR IDENTIFYING AND MONITORING PATIENTS AT RISK FOR SYSTEMIC INFLAMMATORY CONDITIONS, METHODS FOR SELECTING TREATMENTS FOR THESE PATIENTS AND APPARATUS FOR USE IN THESE METHODS

(76) Inventor: Gus J. Slotman, 705 Mill St., Moorestown, NJ (US) 08057

( * ) Notice: Subject to any disclaimer, the term of this patent is extended or adjusted under 35 U.S.C. 154(b) by 0 days.

This patent is subject to a terminal disclaimer.

(21) Appl. No.: 10/321,953

(22) Filed: Dec. 17, 2002

(65) Prior Publication Data

US 2003/0211518 A1 Nov. 13, 2003

Related U.S. Application Data

(63) Continuation-in-part of application No. 09/788,172, filed on Feb. 16, 2001, now abandoned, which is a continuation-in-part of application No. 09/139,189, filed on Aug. 25, 1998, now Pat. No. 6,190,872, which is a continuation-in-part of application No. 08/612,550, filed on Mar. 8, 1996, now abandoned, which is a continuation-in-part of application No. 08/239,328, filed on May 6, 1994, now abandoned.

(51) Int. Cl.
*G01N 33/48* (2006.01)
*G01N 33/86* (2006.01)

(52) U.S. Cl. .......................................... 436/63; 436/69

(58) Field of Classification Search ............... 435/7.92, 435/7, 4, 7.1, 7.4, 811, 967, 973; 436/7.32, 436/7.9, 69, 86, 811, 87; 424/9.2
See application file for complete search history.

(56) References Cited

OTHER PUBLICATIONS

Savino et al. "Routine prophylactic antifungal agents . . . i" Journal of Trauma, vol. 36, No. 1, pp. 20-26, Jan 1994.*
Sauaia et al. ,Archives of Surgery, 129 (Jan. 1994): 39-45).*
Roumen et al. , The Journal of Trauma, 35(3): 349-354, 1993.*
Bone (Annals of Internal Medicine, 115:457-469 (1991) or Clinical Microbiology Reviews, 6(1): 57-68 (Jan. 1993).*
Spriet et al, in ("Good Practice of Clinical Drug Trials", Second Edition, Chapter 6, pp. 53-63, 1997, Karger, NY).*
Bartelink et al (Radiotherapy and Oncology, 50:1-11, 1999).*
Bone, R.C., "The Pathogenesis of Sepsis", *Annals of Internal Medicine* 115:457-469, 1991.
Bone, R.C., "Gram-Negative Sepsis: a Dilemma of Modern Medicine", *Clin. Micro. Rev.* 6(1) :57-68 (1993).
Craddock et al., Complement (C5a)-Induced granulocyte Aggregation in Vitro, *J Clin Invest* 60:260-264, 1977.
Green LC, et al., "Analysis of Nitrate, Nitrite, and [$^{15}N$]*Nitrate in Bilogical Fluids*", Biochem 126:131-138, 1982.
Hammerchmidt et al., "Granulocyte Aggregometry: A Sensitive Technique for the Detection of C5a and Complement Activation", *Blood* 55 (6) :898-902, 1980.
Roumen, R.M. et al., "Scoring Systems and Blood Lactate Concentration in Relation to the Development of Adult Respiratory Distress Syndrome and Multiple Organ Failure In Severely Traumatized Patients", *The Journal of Trauma* 35(3) :349-355; 1993.
Sauaia, A. et al., "Early Predictors of Postinjury Multiple Organ Failure", *Arch Surg.* 129:39-45, 1994.
Slotman et al., "Prostaglandin and Complement Interaction in Clinical Acute Respiratory Failure", *Arch Surg.* 121:271-274, 1986.
Slotman, G.J. et al., "Interaction of Prostaglandins, Activated Complement, and Granulocytes in Clinical Sepsis and Hypotension", *Surgery* 99(6) :744-750, 1986.

* cited by examiner

*Primary Examiner*—Patricia A. Duffy
(74) *Attorney, Agent, or Firm*—Licata & Tyrrell P.C.

(57) ABSTRACT

Methods of identifying, monitoring and matching patients with appropriate treatments who are at risk for developing a systemic inflammatory condition prior to development of signs and symptoms using a systemic mediator-associated physiologic test profile are provided.

1 Claim, 4 Drawing Sheets

METHODS FOR IDENTIFYING AND MONITORING PATIENTS AT RISK FOR SYSTEMIC INFLAMMATORY CONDITIONS, METHODS FOR SELECTING TREATMENTS FOR THESE PATIENTS AND APPARATUS FOR USE IN THESE METHODS

The instant patent application is a continuation-in-part of application Ser. No. 09/788,172, filed Feb. 16, 2001, abandoned in favor of this application, which is a continuation-in-part of application Ser. No. 09/139,189, filed Aug. 25, 1998, now issued as U.S. Pat. No. 6,190,872, which is a continuation-in-part of application Ser. No. 08/612,550, filed Mar. 8, 1996, now abandoned, which is a continuation-in-part of application Ser. No. 08/239,328, filed May 6, 1994, now abandoned.

BACKGROUND OF THE INVENTION

Physiologic insults triggering the onset of systemic inflammatory conditions including sepsis, Adult Respiratory Distress Syndrome (ARDS), Systemic Inflammatory Response Syndrome (SIRS) and Multiple Organ Dysfunction Syndrome (MODS) have been identified to include infection and its systemic effects, shock, trauma, inhalation injury, pancreatitis, hypertransfusion, drug overdose, and near-drowning among others. The host response manifested in each of these insults includes increased capillary permeability, organ failure, and death. The mechanism of the response involves diffuse pathologic activation of inflammatory mediators including, but not limited to, endotoxin, leukotrienes $B_4$, $C_4$, $D_4$ and $E_4$, prostacyclin and thromboxane $A_2$, activated granulocytes and complement components C3a and C5a, tumor necrosis factor, interleukin-1, interleukin-6, interleukin-8, and other cytokines, neutrophil elastase, platelet activating factor, nitric oxide, and oxide radicals.

Bone, R. C. *Annals of Internal Medicine* 115:457-469, 1991, reviews the pathogenesis of sepsis and provides a summary of what is known about mediators involved in this pathogenesis along with a hypothesis for understanding how these mediators produce the endothelial dysfunction believed to be one of the key derangements underlying sepsis. Bone (1991) discloses that sepsis and related disorders result in part from endothelial injury caused by repetitive, localized foci of inflammation which, in turn, produce an increase in capillary permeability. Bone suggests that this endothelial dysfunction is the result of the activities of a series of mediators responsible for the pathogenesis. It is proposed that the release of endotoxin or a comparable substance such as enterotoxin, toxic shock syndrome toxin-1, gram-positive or yeast cell-wall products, and viral or fungal antigens, is the initiating event in the sepsis cascade. Once in the circulation, the substance prompts the release of TNF-α, interleukins, and platelet activating factor. Arachidonic acid is then metabolized to produce leukotrienes, thromboxane $A_2$ and prostaglandins. Almost all of these agents have direct effects on the vascular endothelium. Other suggested agents which may participate in this sepsis cascade include adhesion molecules, kinins, thrombin, myocardial depressant substance, β-endorphin, and heat shock proteins. Bone (1991) presents a pyramid-shaped model of sepsis based upon the theory that the mediators of sepsis can be shown to produce an expanding sequence of events according to the intensity or dose of the original insult. Starting from the top, this pyramid includes (1) infection; (2) release of endotoxin and other bacterial products; (3) release of mediators of inflammation (i.e., cytokines, eicosanoids); (4) sepsis—with or without multi organ failure; (5) sepsis syndrome—with or without multi organ failure; (6) septic shock—with or without multi organ failure; and (7) recovery or death. Bone (1991) suggests that this model may have important implications in the diagnosis and therapy of sepsis.

As a result of identifying causative factors of systemic inflammatory conditions such as sepsis and recent advances in the fields of monoclonal antibodies and recombinant human protein technology, several novel adjuvant treatments have been developed for patients with systemic inflammatory conditions such as sepsis, ARDS, SIRS and MODS. Experimental results and preliminary clinical data suggest that antibodies against gram-negative endotoxin and tumor necrosis factor, human recombinant protein antagonists of interleukin-1 and other cytokines, and inhibitors of platelet activating factor may be beneficial in sepsis, ARDS, MODS and other manifestations of SIRS. Other mediator modifying drugs, such as the cyclo-oxygenase inhibitor ibuprofen, and ketoconazole, a potent antagonist of thromboxane synthetase and 5-lipoxygenase may also be effective in the treatment of ARDS.

Bone, R. C. *Clin. Micro. Rev.* 6(1):57-68 (1993) provides a review of the epidemiology, diagnosis and current management of gram-negative sepsis and examines the therapeutic potentials of new treatments under development. A variety of physiological changes are disclosed which are associated with the development of sepsis including fever, hypothermia, cardiac manifestations, respiratory signs, renal manifestations and changes in mental status. In addition, important aspects of the effective management of sepsis and a review of current management strategies as well as recent advances including immunotherapy are disclosed.

The promise of these new drugs in the treatment of ARDS, sepsis, MODS and SIRS, however, has not been realized in confirmatory trials following pre-clinical and Phase II testing. One of the primary reasons for these therapeutic failures is the inability of investigators to identify specifically patients most likely to benefit from these treatments at an early stage in the host response, before the pathologic mediator activation that causes the systemic inflammatory response is manifested overtly. Accurate subclinical diagnosis and prediction of organ failure, septic shock and gram-negative infection are even less feasible. Consequently, patients are enrolled in prospective investigations of new treatments for ARDS, sepsis, MODS and SIRS using entry criteria that uniformly reflect late, clinically obvious sequelae of the underlying pathophysiologic processes. Studies of potentially beneficial drugs then fail because patients are enrolled after irreversible tissue damage has occurred, or because so many "at risk" patients must be entered to capture the target population that a drug effect can not be demonstrated, or because the spectra of disease entities and of clinical acuity in the study groups are too variable.

The optimal approach to finding new treatments for ARDS, SIRS, MODS, sepsis and related conditions would be to test new therapeutics in specifically identified patients with high power, accurately predicted risk of developing ARDS, SIRS, MODS, sepsis or a related condition at a time when the acute pathophysiology is still subclinical. Although there are several physiologic scoring systems available which measure the severity of illness, the degree of sepsis, the severity of trauma, or the intensity of organ system dysfunction and are used by physicians to identify certain patient populations, these systems are all based upon obvious, late clinical manifestations of the underlying inflammatory phenomena. The predictive power, accuracy, and specificity of these systems, therefore, are limited.

The Injury Severity Score (ISS) was devised in 1974 as an adaptation of the Abbreviated Injury Scale (AIS). The ISS is a measure of the severity of anatomic injury in victims of blunt trauma and has been found to correlate well with mortality. The score is obtained by summing the squares of the three highest values obtained in five body regions, with 0 points for no injury and 5 points for a critical lesion. The ISS is the most widely used system for grading the severity of an injury; however, it has been criticized as there is a systematic under prediction of death and there is no adjustment for age as a risk factor. The Hospital Trauma Index (HTI) is an adaptation of the ISS which contains both anatomic and physiologic elements in six body regions. A good correlation between ISS, HTI and AIS has been shown.

The Glasgow Coma Scale (GCS) was also introduced in 1974 as a simple, reliable and generally applicable method for assessing and recording altered levels of consciousness. Eye opening, best motor response and best verbal response are monitored and scored independently on a scale ranging from 3 (worst) to 15 (best). The GCS has shown good correlation with functional outcome of survivors and therefore has been incorporated into several other scoring systems.

The Trauma Score (TS) was developed in 1980 for rapid assessment and field triage of injured patients. The TS measures physiologic changes caused by injury. It consists of respiratory and hemodynamic information, combined with the GCS. The TS has been shown to have a high predictability of survival and death.

Physiologic (TS) and anatomic (ISS) characteristics are combined in the TRISS scoring method used to quantify probability of survival following an injury. The method was developed for evaluating trauma care but can be applied to individual patients to estimate the probability of survival.

The Sepsis Severity Score (SSS) was developed in 1983 for grading the severity of surgical sepsis. The system consists of a 6-point scale in seven organ systems including lung, kidney, coagulation, cardiovascular, liver, GI tract and neurologic. The final score is calculated by adding the squares of the highest three values of the three organs with the most severe dysfunction. Studies have shown significantly different scores in survivors versus nonsurvivors and the score correlated well with the length of hospital stay in the survivor group.

The Polytrauma Score (PTS), developed in 1985, is an anatomic injury severity score including an age classification. The score is thought to be more practicable than the ISS while having good correlation with the ISS.

The Multiple Organ Failure Score (MOF score), developed in 1985, grades the function or dysfunction of the seven main organ systems including the pulmonary, cardiovascular, hepatic, renal, central nervous, hematologic, and gastrointestinal systems. This score has been shown to correlate well with mortality outcome.

Also in 1985, APACHE II, a revised version of APACHE (Acute Physiologic And Chronic Health Evaluation) was presented. APACHE II is a disease classification system developed to stratify acutely ill patients admitted to the Intensive Care Unit. Increasing scores have been shown to correlate well with hospital death. The score consists of an acute physiology score (APS), and age score, and a chronic health score. The APS is determined from the most deranged physiologic values during the initial 24 hours after ICU admission. The APACHE system, however, has not consistently predicted mortality risk for trauma patients. APACHE III is the latest revision of APACHE but like its predecessors, the system relies only upon clinically evident data and, therefore, is useful only for predicting mortality risk in selected groups of critically ill patients.

In a study performed by Roumen, R. M. et al., *The Journal of Trauma* 35(3):349-355, 1993, the relative value of several of these scoring systems in conjunction with measurement of plasma lactate concentration was examined in relation to the development of ARDS, MODS, or both in patients with severe multiple trauma. It was concluded that scoring systems directly grading the severity of groups of trauma patients have predictive value for late and remote complications such as ARDS and MODS, where as scoring systems that grade the physiologic response to trauma, while related to mortality, have no predictive value.

The scoring systems such as APACHE, TRISS, the Sepsis Score and the Multiple Organ Failure Score rely upon overt clinical signs of illnesses and laboratory parameters obtained after the appearance of clinical signs and, thus, are only useful in predicting mortality in a patient.

A study performed on trauma patients at Denver General Hospital in Colorado (Sauaia, A. et al., *Arch Surg.* 129:39-45, 1994) found that early independent predictors of postinjury multiple organ failure include age greater than 55 years, an Injury Severity Score greater than or equal to 25, and receipt of greater than 6 units of red blood cells in a 12 hour period. Subgroup analysis indicated that base deficit and lactate levels could add substantial predictive value.

Clinical application of any of these prior art scoring systems has been limited to an assessment of grouped percentage risk of mortality. None of the systems are applicable to individual patients. Furthermore, being limited only to predicting risks of hospital death, and possibly consumption of health care resources, the currently variable prognosticated systems can only categorize patients with similar physiology into like mortality risk groups; the systems do not predict important pathophysiologic events in individual patients that could facilitate timely therapeutic intervention and improve survival.

In order for pathophysiologic prognostication to become clinically beneficial to individual patients, a system must predict subclinically the physiologic insults and sequelae of systemic inflammation that lead to mortality in advance so that data-based interventions can be administered in a timely fashion and survival can be optimized. A key to achieving this new level of critical care prediction is to recognize temporal pathophysiology links between baseline clinical and subclinical data and subsequent events in the clinical course of individual patients.

In the present invention, methods are provided for predicting subclinically, meaning prior to development of signs and symptoms which are diagnostic, a patient's risk for developing a systemic inflammatory condition such as ARDS, SIRS, sepsis and MODS, and predicting their response to a selected therapeutic agent. The methods of the present invention are based upon predictive models or profiles, referred to herein as the Systemic Mediator Associated Response Test (SMART), which are generated for a patient and then compared to established baseline values or to a patient's normal values to predict a patient's risk of developing a systemic inflammatory condition and to match the patient with an appropriate treatment for the condition.

SUMMARY OF THE INVENTION

An object of the present invention is to provide a method of subclinically identifying patients at risk for developing a systemic inflammatory condition prior to development of signs and symptoms which permit diagnosis of the selected systemic inflammatory condition which comprises generating and comparing a systemic mediator-associated response test (SMART) profile for the patient with an established control profile to identify patients at risk of developing a systemic inflammatory condition based on the comparison. SMART profiles of the present invention are generated from various selected patient parameters including, but not limited to, selected demographic variables, selected physiologic variables and/or standard hospital laboratory tests. The diagnostic and predicted accuracy of the SMART profile is provided by serial measurements of physiologic variables which are compared to clinical database profile patterns of change related to the development of a systemic inflammatory condition. Treatment of patients at risk of developing a systemic inflammatory condition can be evaluated by monitoring changes in a patient's SMART profile.

Another object of the invention is to provide a method of quantitatively predicting selected patient parameters in a patient having or at risk for a selected systemic inflammatory condition which comprises generating a systemic mediator-associated response test profile for the patient from selected patient parameters, comparing said profile with an established control profile, and predicting selected patient parameters in the patient based upon the comparison.

Yet another object of the present invention is to provide a method of monitoring changes in selected patient parameters in a patient to assess a treatment of a systemic inflammatory condition which comprises generating a systemic mediator-associated response test profile for the patient from selected patient parameters, monitoring changes in one or more selected patient parameters in the profile, and comparing any changes in the profile with an established control profile to monitor treatment of a systemic inflammatory condition.

Yet another object of the present invention is to provide a method for matching treatments with patients at risk for developing a systemic inflammatory condition which comprises generating a systemic mediator-associated response test (SMART) profile for the patient from selected patient parameters, and comparing this profile with established control profiles for treatments to match a treatment with the patient based on the comparison. This method of matching patients with treatments can be used to select effective treatments for a patient as well as for selecting an appropriate patient population for testing of new drugs being developed for use in treatment of systemic inflammatory conditions.

BRIEF DESCRIPTION OF THE FIGURES

FIG. 1a provides a topview of the injecting grid. FIG. 1b provides a side view of the injecting grid.

FIG. 2a provides a top view of the reagent grid. FIG. 2b provides a side view of the reagent grid.

FIG. 3a provides a top view of the antibody grid. FIG. 3b provides a side view of the antibody grid.

FIG. 4a shows a first position wherein the compression injecting grid is kept separate from the reagent grid by a circumferential spacing band. FIG. 4b shows a second position wherein the circumferential spacing band has been removed.

DETAILED DESCRIPTION OF THE INVENTION

Figure 1A:
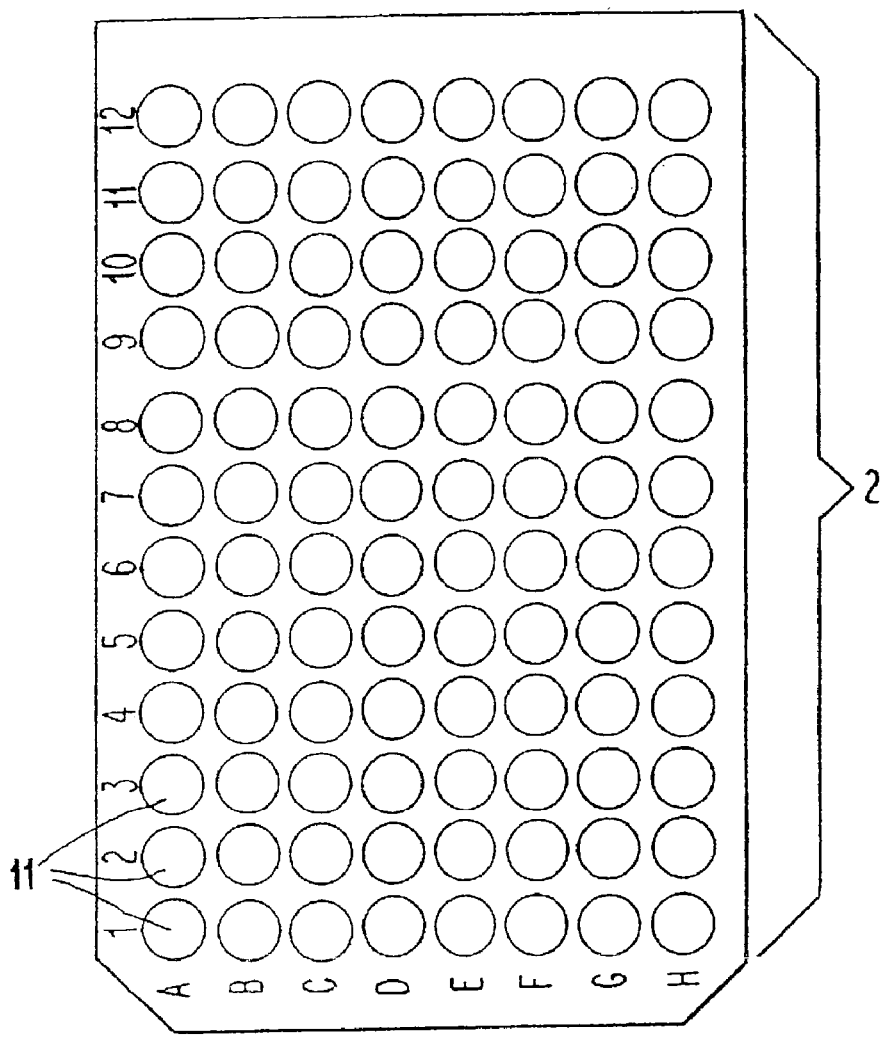
FIGS. 1a and 1b show the injecting grid of the multiple analysis grid for grouped independent ELISAs.

The development of systemic inflammatory conditions represents a significant portion of the morbidity and mortality incidence which occur in the intensive care unit (ICU). The term "systemic inflammatory conditions" is used herein to describe conditions which result in a host response manifested by increased capillary permeability, organ failure, and death. Examples of systemic inflammatory conditions include, but are not limited to, ARDS, SIRS, sepsis, MODS, single organ dysfunction, shock, transplant rejection, cancer and trauma. Systemic inflammatory conditions such as ARDS, SIRS and MODS are responsible for more than 70% of the ventilator days spent on the ICU. In addition, ARDS, SIRS, sepsis and MODS are primary causes of death following surgery in surgical ICU patients, thus placing a heavy burden on the health care system.

It is believed that systemic inflammatory conditions, particularly ARDS, SIRS and MODS, are the result of a severe generalized autodestructive inflammation. ARDS is manifested clinically by hypoxemia, hypocapnia, diffuse infiltrates on chest roentgenogram and normal or low left ventricular filling pressures. Circulating prostaglandins, activated complement and abnormal intravascular aggregation of neutrophils have been implicated as possible mediators of ARDS. Slotman et al., $Arch\ Surg.$ 121:271-274, 1986. Thromboxane $B_2$ (TxB), prostaglandin 6-keto-Fl$\alpha$ (PGI), activated complement components C3a and C5a, and granulocyte aggregation (GA) were found to be significantly elevated in all critically ill patients as compared to normal controls. For patients with ARDS the ratios of TxB/PGI and C3a/C5a also were significantly greater than controls. Differences between patients with and without ARDS in this study, however, were significant only for increased GA and plasma C3a in ARDS.

Circulating prostaglandins, activated complement, and pathologic neutrophil aggregation are also involved in the clinical response to injury and infection and in the hemodynamic dysfunction of septic and hypovolemic shock. PGI, activated complement components C3a and C5a, and GA responses were significantly increased in critically ill patients as compared to normal control values. Slotman, G. J. et al., $Surgery$ 99(6):744-750, 1986. TxB levels were also found to be significantly elevated in patients with severe sepsis and septic shock.

Treatments for systemic inflammatory conditions have failed to reach their full potential as early subclinical identification of appropriate patients to participate in clinical efficacy studies has proven most difficult. Physiologic scoring systems which are used by physicians to predict mortality in a patient have generally proven insufficient in predicting the onset of a systemic inflammatory condition subclinically.

In the present invention a method of identifying patients at risk for developing a systemic inflammatory condition prior to development of signs and symptoms which permit diagnosis of the selected systemic inflammatory condition is provided. This method comprises generating a Systemic Mediator-Associated Response Test (SMART) profile for the patient from selected patient parameters. The SMART profile is then compared with an established control profile to identify subclinically patients at risk of developing a systemic inflammatory condition based on the comparison. Prior to development of signs and symptoms which permit diagnosis of disease is also termed "subclinical". Thus, for the purposes of the present invention, subclinical identification does not precede the development of all symptoms but rather only those which permit a diagnosis of the disease. With systemic inflammatory conditions, by the time a diagnosis can be made based upon the manifest symptoms, irreversible tissue damage has already occurred. Accordingly, the present invention meets a long felt need for a method of subclinically identifying patients at risk for developing the condition. SMART profiles of a patient can be generated whenever a physician believes, based upon his or her own clinical judgment, that a patient may be at risk of developing a systemic inflammatory conditions. Generally, systemic inflammatory conditions do not develop in healthy individuals but rather in patients with preexisting severe disease or in persons who have suffered catastrophic acute illness or trauma. Patients at greatest risk of dying of a systemic inflammatory condition are the elderly; those receiving immunosuppressive drugs; and those with malignancies, cirrhosis, asplenia, or multiple underlying disorders. Bone, R. C. *Annals of Internal Medicine* 115:457-469, 1991. Accordingly, SMART profiles for patient in this high risk group would be especially useful to clinicians. Once a patient is identified as "at risk", the physician would employ their experience and judgment in determining the appropriate mode and timing of treatment.

The SMART profiles can also be used in the quantitative prediction of concentrations of mediators produced during the host inflammatory response. The course of acute inflammatory mediators involved in a systemic inflammatory condition such as clinical sepsis can be prognosticated through the integration of physiologic variable and subclinical reactants by the SMART profile.

A method is also provided for monitoring changes in selected patient parameters in patients to evaluate a treatment of a systemic inflammatory condition. In this method a SMART profile is generated for the patient based upon selected patient parameters. The patient is then monitored for any changes in the patient parameters from said profile in a response to a treatment. In addition, the changes in the profile are compared with an established control profile to monitor the treatment of patients at risk of developing a systemic inflammatory condition based on the comparison.

Methods are also provided for matching patients with treatments based upon comparison of SMART profiles for the patient and established control profiles for effective treatments or new treatments in development. By matching patients with treatments, effective treatments for patients at risk for developing a systemic inflammatory condition can be selected. In this method, a SMART profile is generated for the patient from selected patient parameters. The patient SMART profile is then compared with established control profiles for effective treatments. Selection of a treatment for the patient is based upon comparing and identifying the established control profiles for effective treatments which exhibit similarities to the patient's profile. In addition, appropriate patient populations for testing of new drugs in development can be selected via matching of patients with treatments based upon SMART profiles. By "appropriate patient population" it is meant subjects who meet the clinical entry criteria of a study for a new drug and who were ready biologically to respond to the new drug if randomized to it.

For purposes of this invention, a "control profile" can either be generated from a data base containing mean values for selected patient parameters from a population of patients with similar conditions and/or injuries or profiles of changing parameters associated with a similar condition and/or injury, or can be generated from the same patient to compare and monitor changes in the patient parameters over time.

By "control profile for effective treatment" it is meant that the control profile, as defined supra, is linked to a treatment identified to be effective in those patients with similar conditions and/or injuries from which the control profile was generated.

SMART profiles of the present invention are generated from one or more patient parameters. Patient parameters, for purposes of this invention, may include selected demographic variables, selected physiologic variables and/or results from selected standard hospital laboratory tests.

Exemplary demographic variables which may be selected for inclusion in a SMART profile include, but are not limited to, age, sex, race, comorbidities such as alcohol abuse, cirrhosis, HIV, dialysis, neutropenia, COPD, solid tumors, hematologic malignancies, chronic renal failure and the admitting service, i.e. surgery or medicine, and trauma.

Examples of physiologic variables which may be selected for inclusion in a SMART profile include, but are not limited to, physical examination, vital signs, hemodynamic measurements and calculations, clinical laboratory tests, concentrations of acute inflammatory response mediators, and endotoxin levels. More specifically, physiologic variables selected may include height, weight, temperature, MAP, heart rate, diastolic blood pressure, systolic blood pressure, mechanical ventilation, respiratory rate, pressure support, PEEP, SVR, cardiac index and/or PCWP of the patient. In addition, complete blood count, platelet count, prothrombin time, partial thromboplastin time, fibrin degradation products and D-dimer, serum creatinine, lactic acid bilirubin, AST, ALT, and/or GGT can be measured. Heart rate, respiratory rate, blood pressure and urine output can also be monitored. A full hemodynamic profile can also recorded in patients with pulmonary artery catheters and arterial blood gases are performed in patients on ventilators. Chest X-rays and bacterial cultures can also performed as clinically indicated. Examples of inflammatory response mediators which can be determined from a biological sample obtained from the patient include, but are not limited to, prostaglandin 6-keto Flα (PGI)(the stable metabolite of prostacyclin), thromboxane $B_2$ (TxB) (the stable metabolite of thromboxane $A_2$), leukotrienes $B_4$, $C_4$, $D_4$ and $E_4$, interleukin-6, interleukin-8, interleukin-1, tumor necrosis factor, neutrophil elastase, complement components C3 and C5a, platelet activating factor, nitric oxide metabolites and endotoxin levels.

Exemplary hospital laboratory tests considered standard by those skilled in the art which may be selected for inclusion in a SMART profile include, but are not limited to, levels of albumin, alkaline phosphatase, ALT, AST, BUN, calcium, cholesterol, creatinine, GGT, glucose, hematocrit, hemoglobin, MCH, MCV, MCHC, phosphorus, platelet count, potassium, total protein, PT, PTT, RBC, sodium, total bilirubin, triglycerides, uric acid, WBCL, base deficit, pH, $PaO_2$, $SaO_2$, $FiO_2$, chloride, and lactic acid.

Some or all of these patient parameters are preferably determined at baseline, and daily thereafter where applicable, and are entered into a database and a SMART profile comprising one or more of the patient parameters is generated from the database. As one of skill in the art will appreciate upon this disclosure, as other additional patient parameters are identified which are predictive of a systemic inflammatory condition, they can also be incorporated into the database and as part of the SMART profile. Similarly, as SMART profiles are generated for more patients and additional data are collected for these parameters, it may be found that some parameters in this list of examples are less predictive than others. Those parameters identified as less predictive in a larger patient population need not be included in all SMART profiles.

Examples of biological samples from which some of these physiologic parameters are determined include, but are not limited to, blood, plasma, serum, urine, bronchioalveolar lavage, sputum; and cerebrospinal fluid.

PGI, TxB, and the leukotrienes $B_4$, $C_4$, $D_4$ and $E_4$ are derived from polyunsaturated fatty acids via arachidonic acid. These molecules play an important role in smooth muscle contraction, affecting blood pressure, blood flow, the degree of bronchial constriction and uterine contraction. Thromboxane is a potent vasoconstrictor and enhancer of platelet aggregation. Other prostaglandins and the leukotrienes promote the inflammatory response. Leukotrienes act as chemotactic agents, attracting leukocytes to the site of inflammation. Tumor necrosis factor α (TNFα) is a cytokine primarily produced by activated macrophages. TNFα stimulates T-cell and B-cell proliferation and induces expression of adhesion molecules on endothelial cells. This cytokine also plays an important role in host defense to infection. Platelet activating factor mediates platelet homeostasis and interacts with cytokines such as TNFA. Imbalances in PAF can result in uncontrolled bleeding or clot formation and a shock-like hemodynamic and metabolic state. The interleukins 1β, 6, and 8 and complement components C3a and C5a also play a major role in host defense to infection and in the host inflammatory response. Increased cytokine and complement levels in a patient are indicative of an infection and/or inflammation. Neutrophil elastase is an enzyme which hydrolyzes elastin. Elastin is a fibrous mucoprotein that is a major connective tissue protein in tissues with elasticity. Nitric oxide helps to regulate smooth muscle tone possibly through interaction with the prostaglandins and cytokines. The presence of increased nitric oxide metabolites in a biological sample may be indicative of an imbalance in protein degradation or impairment of renal function in a patient. The presence of endotoxin in a biological sample obtained from the patient is indicative of a gram negative bacterial infection. Such infections can lead to the development of shock in a patient. Pathological imbalances of the dynamic equilibrium among these and other biologically active substances cause endothelial damage, increased capillary permeability, and the cascade of subclinical events that leads to systemic inflammatory conditions such as sepsis, ARDS, SIRS, and MODS.

In order to determine levels of these multiple biochemical and cellular inflammatory mediators simultaneously for use in generation of a SMART profile, methods routinely used in automated immunoassay machines are useful. These include, but not be limited to ELISA assays. In one embodiment of the present invention, a multiple analysis grid for grouped independent ELISAs (MAGGIE) was developed which can be used to determine levels of multiple biochemical and cellular inflammatory mediators simultaneously for use in generation of a SMART profile. FIGS. 1a, 1b, 2a, 2b, 3a, 3b, 4a, and 4b illustrate a preferred embodiment of MAGGIE 1.

Referring now in specific detail to the drawings, this grid 1 comprises a conventional 96 test well format having three planar, superposed and contacting grids: an injecting grid 2, a reagent grid 3 and an antibody grid 5.

Figure 3A:
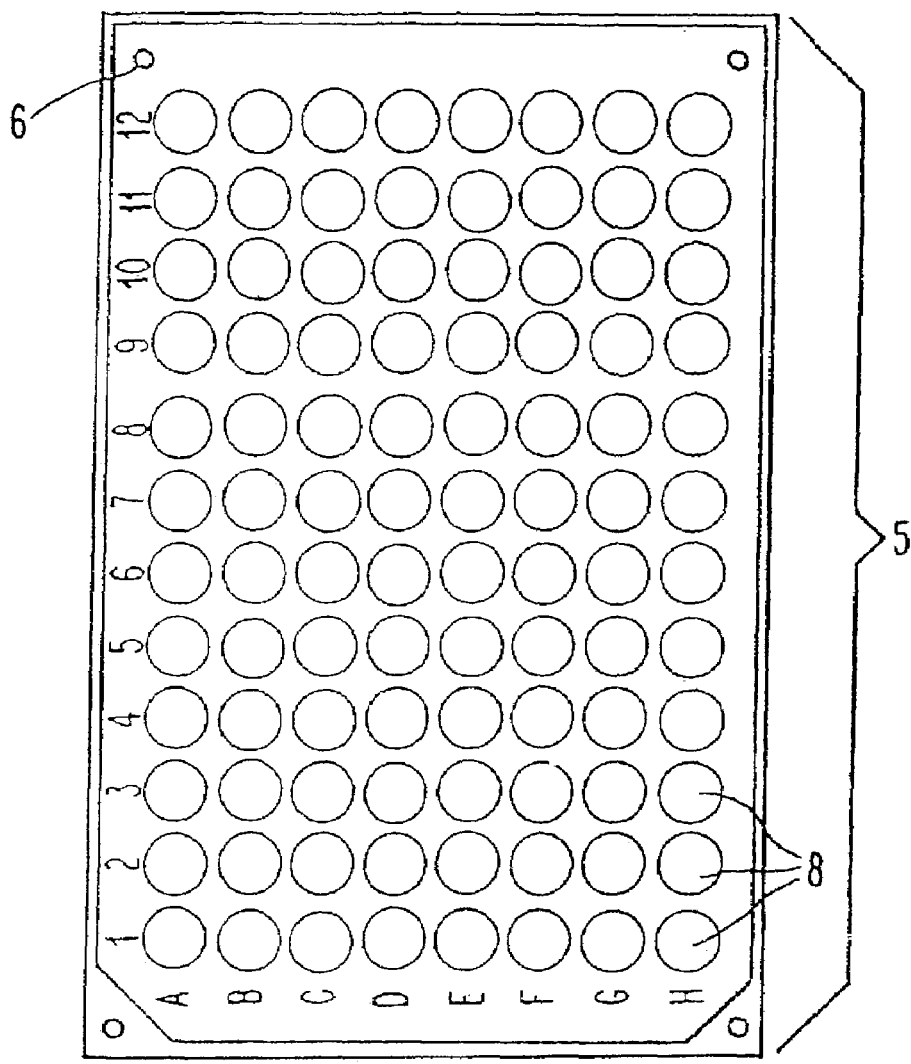
FIGS. 3a and 3b show the antibody grid which serves as the base of the multiple analysis grid for grouped independent ELISAs.
Figure 3B:
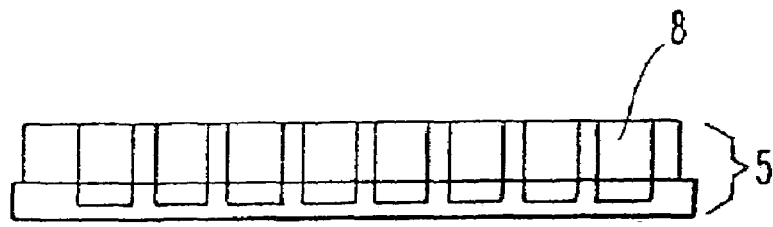

The antibody grid 5 as shown in FIGS. 3a and 3b comprises an 8×12 array of test wells 8 having antibodies coated thereupon, a receiving hole 6 at each of its four corners and a removable plastic cover over five rows of test wells 8. In a preferred embodiment, each of the 12 columns of the antibody grid 5 are capable of measuring a different biochemical or cellular inflammatory mediator. Further, it is preferred that in each column, wells A, B, C, and D contain known quantities of the mediator to be analyzed and will constitute the standard curve for that assay. In this embodiment, well E in each column contains a known quantity of the mediator to be analyzed, in a concentration taken from the mid-point of the standard curve, the reading of which will determine the percent recovery of the assay, as an inter-assay method of quality control. Wells F, G and H each in each column will receive the sample to be analyzed against the standard curves of wells A-D in that column.

Figure 2A:
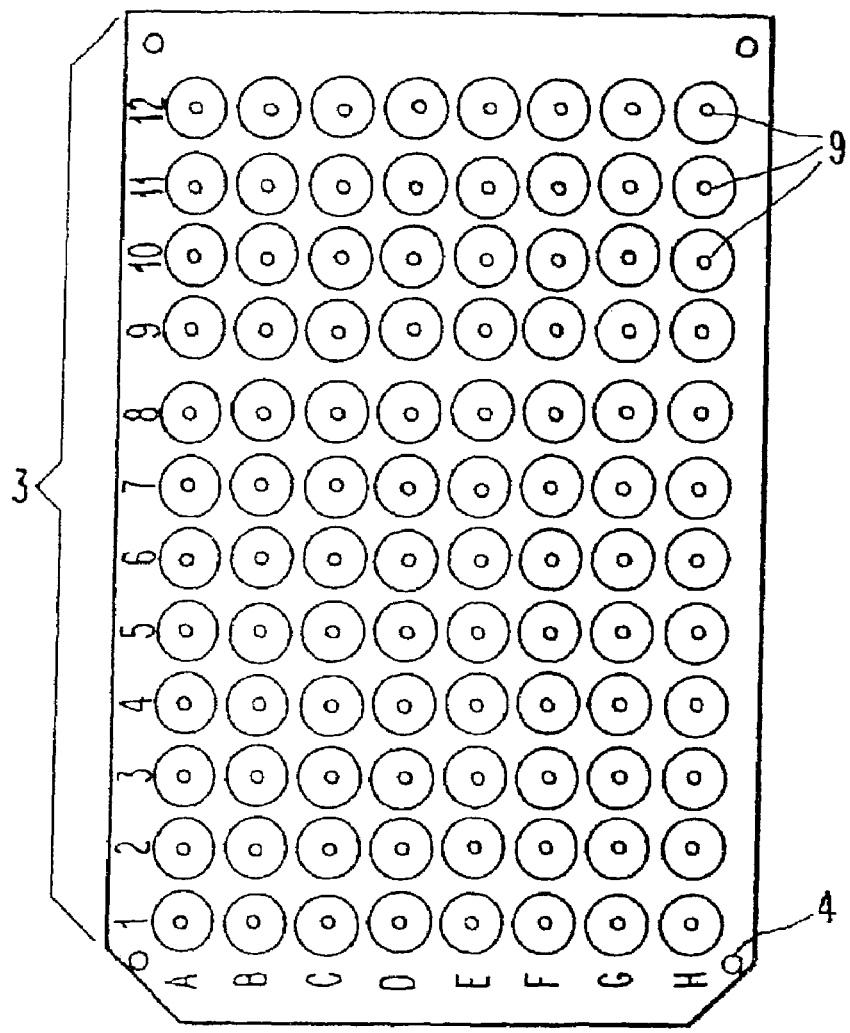
FIGS. 2a and 2b show the reagent grid with perforating micropipettes of the multiple analysis grid for grouped independent ELISAs.
Figure 2B:
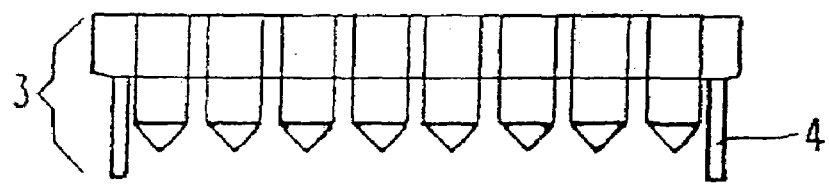

The reagent grid 3 as shown in FIGS. 2a and 2b comprises a 96 well array and locking posts 4 at its corners such that the wells 9 and locking posts 4 align to form a superposed arrangement with the antibody grid 5. Reagent grid wells 9 contain suitable assay reagents and holes at their lowermost ends, said holes being covered with a plastic film to prevent reagent leakage from the reagent wells prior to use.

Figure 1B:
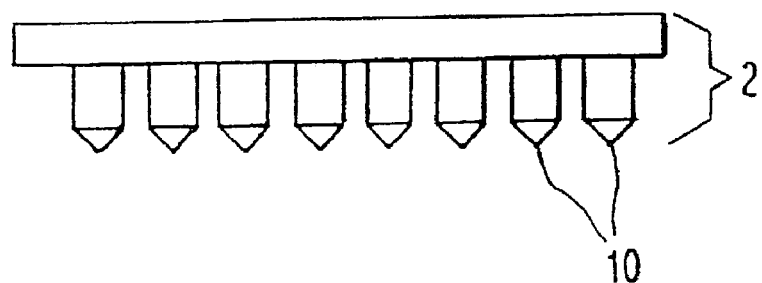

The injecting grid 2 as shown in FIGS. 1a and 1b comprises a 96 plunger array adapted for insertion into respective reagent wells from above, said plungers 10 having a sealed piston relationship with the cylindrical walls of said reagent wells 11 when inserted therein.

Figure 4A:
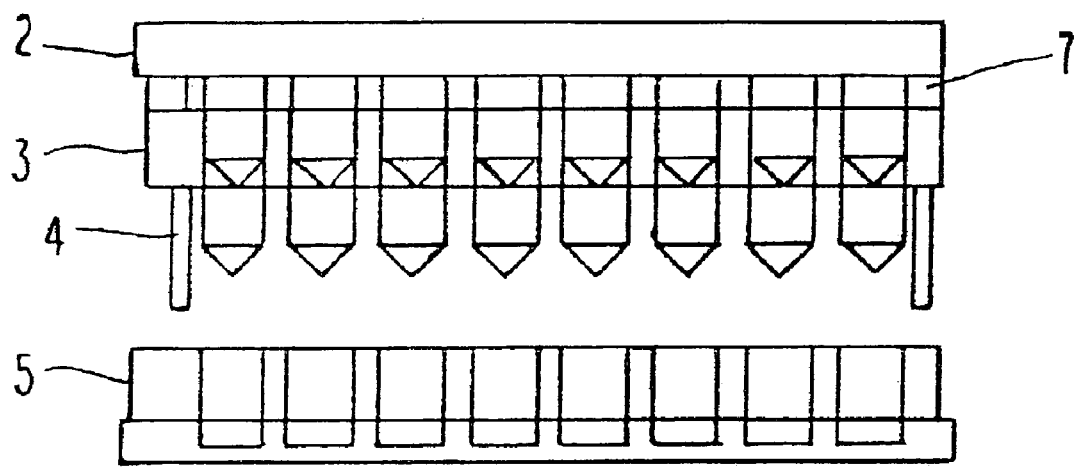
FIGS. 4a and 4b provide a side view of the multiple analysis grid for grouped independent ELISAs wherein the injecting grid, the reagent grid and antibody grid are assembled.
Figure 4B:
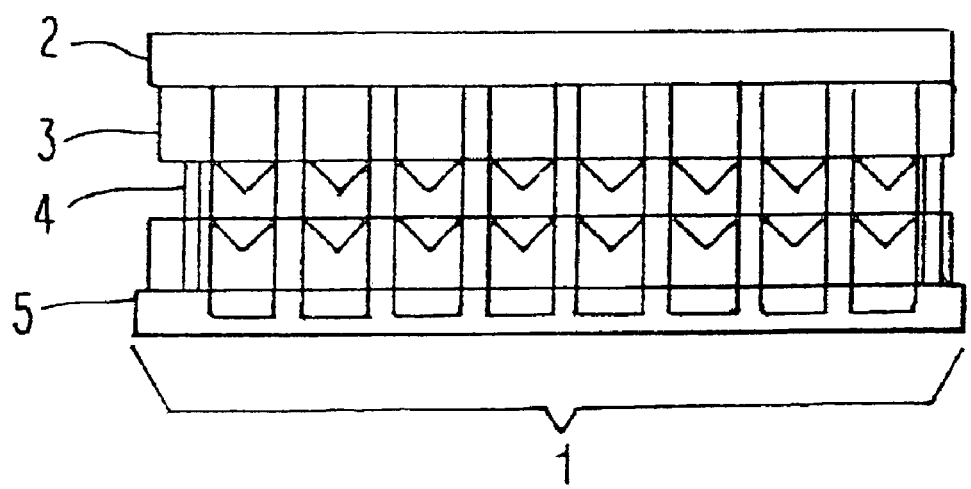

In use, a sample from a patient believed to be at risk for developing a systemic inflammatory condition is aliquoted into the antibody grid wells 8 F-G and the plastic cover is removed from the other rows of wells. The plastic film on the reagent grid 3 is then removed from the reagent grid 3 along with the circumferential spacing band 7 between the reagent grid 3 and injector grid 2 to form a reagent-injector assembly as shown in FIGS. 4a and 4b. This assembly is then superposed onto the antibody grid 5 and the injector grid 2 is depressed in order to expel the contents of the reagent grid wells 9 into the antibody grid wells 8 to initiate the multiple ELISA reactions. Accordingly, in this embodiment, the multiple analysis grid for grouped independent ELISAs of the present invention can be used to measure multiple mediators in a patient sample simultaneously.

For example, in one embodiment, the antibody grid can be arranged to measure $PGI_2$ in column 1, $TxB_2$ in column 2, $LTB_4$ in column 3, $LTC_4$, $D_4$ and $E_4$ in column 4, TNFα in column 5, IL-1β in column 6, IL-6 in column 7, IL-8 in column 8, PAF in column 9, elastase in column 10, and endotoxin in column 11.

As will be obvious to those of skill in the art, however, the mediators to be measured can be altered or arranged in various fashions.

It is preferred that the multiple analysis grid for grouped independent ELISAs be provided as a kit comprising an antibody-loaded standard 96-well ELISA analysis plate as the antibody grid, a reagent grid preloaded with reagents corresponding to the antibody grid for the ELISA assay, and an injecting grid which transfers the reagents from the reagent grid onto the antibody grid. In packaging, after the holes in the reagent grid wells have been sealed and wells filled with reagents appropriate to the standard curve (rows A-D), spiked control (row E), and sample analysis (rows F-H), the tips of the injector grid columns are placed inside the matching reagent grid wells. A circumferential spacing band is placed between the outer plates of each grid to prevent premature release of reagents from the reagent grid. The assembly is held together by plastic bands placed around the injector grid/reagent grid assembly.

As will be obvious to those of skill in the art upon this disclosure, however, other means for measuring the selected mediators can also be used.

As will be understood by those of skill in the art upon reading this disclosure, prediction of the patient's risk of developing a systemic inflammatory condition can be based upon a SMART profile comprising all of the various patient parameters discussed supra. Alternatively, these predictions can be based upon a SMART profile comprising only a portion of the patient parameters. Since the patient parameters for each patients, as well as the control profiles, are stored in a database, various SMART profiles comprising different patient parameters can be generated for a single patient and compared to an established control profile comprising the same parameters. The predictiveness of these various profiles can then be determined via statistical analysis. For example, comparison of a SMART profile comprising only demographics and standard hospital laboratory tests to established control profiles comprising these same parameters has been found to be predictive of risk. See Example 9 and 10.

Continuous, normally distributed variables are evaluated using analysis of variance. Where appropriate, statistical comparisons between subgroups are made using the t-test or the chi-squared equation for categorical variables. Relative risks of developing sepsis or multiple organ failure are computed using a least square regression and logistic regression.

The physician or another individual of skill in the art uses the predictions of the SMART profile as a guide to identifying patients at risk for developing a systemic inflammatory condition prior to development of clinical symptoms of the systemic inflammatory condition. By comparing the SMART profile generated from selected patient parameters, the patient can be categorized by severity of the signs and symptoms, and the presence of systemic inflammatory disease progression or potential development identified.

For example, in a first set of experiments, a retrospective analysis was performed to determine whether circulating levels of eicosanoid mediators of inflammation, physiologic measurements and standard clinical laboratory results are of inflammation and organ failure in patients with severe sepsis. Seventy-three patients admitted to the Intensive Care Unit and/or Emergency Department who were subsequently diagnosed as septic were studied. Clinical data collected at the time of admission, referred to hereinafter as "baseline" data, included Glasgow Coma Score, systolic, diastolic and mean arterial blood pressures, respiratory rate and urine output. Routine clinical laboratory measurements included serum BUN, creatinine, bilirubin, AST, and arterial blood gas ($PaO_2$, $HCO_3$, $SaO_2$ and $PaO_2/FiO_2$ ratio). Minimum platelet count and maximum prothrombin time for each 24-hour period was measured also. Vital signs, physical examination and clinical laboratory data were obtained at baseline and daily for days 1-7 and then repeated if the patient was available on days 14, 21 and 28 of observation. In addition, aliquots of blood were collected from each patient at baseline to determine levels of thromboxane $B_2$ ($TXB_2$), prostaglandin 6-keto-F 1-$\alpha$ ($PGI_2$), leukotriene $B_4$ ($LTB_4$), leukotrienes $C_4$, $D_4$, $E_4$ ($LTC_4$, $LTD_4$, $LTE_4$), interleukin-1 $\beta$ (IL-1), interleukin-6 (IL-6), and tumor necrosis factor (TNF).

For the observed physiologic and clinical laboratory parameters, the most pathologic value noted from baseline through 28 days was determined. Maximum values were collected for Glasgow Coma Score, the Murray Scale for acute respiratory failure, serum creatinine, bilirubin, AST and prothrombin time. The lowest observed measurement was recorded for systolic, diastolic, and mean arterial pressures, platelet count, and arterial blood gas parameters of $pO_2$, $SaO_2$, $HCO_3$ and $PaO_2/FiO_2$ ratio.

Clinically significant interactions were first determined by pair-wise correlation matrix analysis using, for example, cross correlation analysis, log transformation plus cross correlation and non-parametric cross correlation. The most significant cross correlations were then subjected to linear regression analysis and, finally, multivariate analysis to establish predictive models for survival time, pulmonary dysfunction, renal dysfunction, hepatic dysfunction, cerebral dysfunction and disseminated intravascular coagulation (DIC). Once the predictive model for each indicator was established, its accuracy was tested retrospectively by recalculating a predicted organ function indicator level from its derived equation and plotting these values against the data actually observed. Scores for each parameter in each patient were then ranked and divided into septiles of approximately 10 values each. Then, defining the adult respiratory distress syndrome (ARDS) as a Murray score of 7 or greater, and defining hepatic, renal or cerebral dysfunction and DIC, the percent of the patients in each septile of predicted scores for end-organ failure and for survival time were plotted against the percentage of that septile which developed the target condition at baseline or anytime thereafter, up to 28 days. For survival time, septile of decreasing severity were plotted against survival time in days.

A strong correlation of prothrombin time predicted by the SMART profile versus observed values was evident. A similar strong interaction between predicted creatinine, which includes the log of $PGI_2$, and observed maximum creatinine levels in septic patients over the creatinine range of 0 to 4 mg/dl was observed. The septiles of increasing creatinine score were also plotted against the percent of patients in each septile who developed acute renal failure from baseline through 28 days and a linear relationship of ascending SMART profile renal failure score and the incidence of subsequent renal failure was observed. Cerebral dysfunction, as defined by a Glasgow Coma Scale of less than 9, was also observed with progressively increasing frequency as the SMART profile score for cerebral dysfunction increased. A linear relationship between predicted and observed $SaO_2$ was also seen within the physiologically important range of 85 to 100% $SaO_2$. In addition, a strong relationship between the SMART profile's maximum Murray score and that actually observed in the 73 patients was seen. Over the range of 1 to 12 on the Murray scale, the fit of the predictive equation, which includes $PGI_2$ and $TXB/PGI_2$ interactions, among others, has a linear relationship. Over 62% of the variation in the observed Murray values was accounted for by the SMART method. This is most significant, considering the small number of patients involved and the fact that only seven subclinical inflammatory response mediators were measured at baseline.

Further, a direct relationship between decreasing severity of the SMART profile's survival time score with increasing mean survival time was seen thereby demonstrating that, overall, the SMART method indicates not only percentage risk of developing a systemic inflammatory condition but quantitative survival time for the 28 day period after baseline, as well.

Linear regression analysis was also performed for 59 of the 73 patients with sepsis syndrome on whom $TxB_2$, $PGI_2$, $LTB_4$, $LTC_4$, $LTD_4$, $LTE_4$, IL-1, IL-6, and TNF alpha levels, in addition to a completed battery of physiologic indicators of organ failure were measured. Multivariate regression equations were developed using baseline mediator levels and the worst organ system physiology exhibited in each patient. The predicted outcome versus the observed outcome was then plotted for each parameter. The SMART multivariate regression equations account for 17.1% to 90.4% of the variability of each parameter in this study. Statistically, the percent of variation accounted for by SMART equations will increase toward 100% as the total number of patients in each group increases.

The actual values and values predicted by SMART for a number of physiologic parameters in these 59 patients were compared at 24 hours, 48 hours and 72 hours after baseline determination. The predicted values for each patient at 24, 48 and 72 hours were determined by SMART based upon baseline measurements in each patients. Statistically relevant correlations were seen between the predicted values by SMART profiles and the actual values measured.

Accordingly, SMART profiles establish a baseline for levels of these parameters in patients having a systemic inflammatory disease such as sepsis and serve as a control for comparison in identifying patients at risk for developing the disease. The profile from a patient who has not been diagnosed can be compared to profiles from patients diagnosed with a systemic inflammatory disease, such as sepsis, to determine whether similar trends are seen in the measured parameters. This profile comparison, in combination with other methods routinely used, can be used to make an earlier and more definitive determination of those at risk for these conditions. The integration of physiologic variables and subclinical reactants through generation of a SMART profile was also found to be useful in predicting levels of circulating inflammatory mediators in patients. Clinical observations, standard laboratory tests and plasma eicosanoid and cytokine levels recorded prospectively in 24 adults with sepsis syndrome were analyzed retrospectively. Baseline data were used to develop a multivariate regression model that predicted acute inflammatory response mediator blood concentrations up to 72 hours in advance. Predicted plasma levels versus observed measurements for $TxB_2$, PGI, $LTB_4$ and $LTC_4$, $LTD_4$, $LTE_4$, IL-1, IL-6 and TNF were compared using linear regression analysis. It was found that predictions made using baseline data correlated well with actual observed levels. Accordingly, the SMART profiles of the present invention provide a means of prognosticating the course of acute inflammatory mediators in systemic inflammatory conditions. Further validation experiments of the SMART profile system were performed in patients with severe sepsis or septic shock enrolled in a clinical trial. The results of these experiments are presented in Example 9.

SMART profiles were also applied to a database generated from a second phase III clinical trial of the E5 anti-endotoxin antibody with the objective of identifying subjects who met the clinical entry criteria of the study and who were ready biologically to respond to the active E5 if randomized to it. Using multivariate stepwise logistic regression techniques, SMART profiles were developed that predicted which patients were most likely to respond to the active antibody. Baseline data tested included demographics, physiologic observations, hospital laboratory tests, and plasma levels of endotoxin and cytokines. In these experiments, SMART profiles were first developed separately from the placebo and from active E5 baseline databases. Logistic regressions were also developed to determine which independent variables contributed to the dichotomous dependent variables death and organ failure and/or death. The patients were separated by treatment group and one logistic regression model was developed using patients receiving the E5 treatment and a second logistic regression model was developed for the placebo patients. Independent variables for both models were selected by stepwise selection with all ways elimination. Both of the logistic regression models created two possible probabilities for each patient; the probability of survival for the patient receiving E5 and the probability of survival for the patient receiving placebo. Possible cut-offs for the probabilities were examined to determine which patients would have the best survival if they received E5, and which would recover independent of treatment if they received placebo. Examining different cohorts of patients with Kaplan-Meier survival models determined the cut-off. Exploration into the relationships between SMART predictive models and outcomes of E5 and placebo study arm patients resulted in a model that predicted an 80% probability of treatment success for subjects who received E5. In addition, research subjects who had been entered into the E5 study, and who were predicted by the final SMART models to be E5 responders were randomized to placebo and active drug. Kaplan-Meier survival analyses then were performed comparing the results of E5 versus placebo. Treatment effects of E5 on organ/failure death were also analyzed on these same groups.

The first signs of an E5 treatment effect were evidenced by differences in the weighted independent variables for SMART models developed from the E5 versus the placebo databases. In survival modeling, for example, weighted independent variables for the placebo cohort included APACHE II score, urinary tract infection, respiratory tract infection, diastolic, blood pressure, and the presence/absence of DIC. The models for the active E5 cohort were quite difference, and included APACHE II score, age, neurologic conditions, acute central nervous system dysfunction, ARDS, DIC, and hepatobiliary failure as weighted independent variables. The ROC AUC for the E5 survival model was 0.810, indicating very good prognostic discrimination between outcomes.

Exploration into the relationship between the placebo and active E5 models and their interactions with the treatment effects observed in the two study arms revealed a SMART profile predictive of an 80% probability of treatment success if the patient received E5 and capable of identifying at pre-randomization baseline those subjects who are suited biologically to respond to E5. Baseline data from 759 evaluable patients enrolled in a parent study were then entered into this SMART profile, resulting in a study population of 388 patients who were predicted to respond to E5 if they received active drug. These subjects were then analyzed as placebo or active E5 according to their actual randomization into the parent study. In the parent study (n=759), placebo mortality was 27.4% and E5 was 26.2%. This was a 1.2% absolute and a 4.4% relative reduction in mortality by E5 (p=0.747). Among the 388 subjects who fit the SMART profile for E5, mortality in the placebo cohort was 17.1%. For the E5 group, mortality was 8.0%. This absolute 9.1% reduction in mortality by E5 translated into a 53.2% relative reduction, statistically significant at the p=0.006 level.

SMART identification of subjects appropriate for E5 beneficially influenced the active drug's effect on organ failure as well. As shown in the following table, E5 versus placebo p values for ameliorating organ failure/death were reduced dramatically in the SMART population.

| P Values | All (n = 759) | SMART (n = 388) |
|---|---|---|
| ARDS | 0.43 | 0.01 |
| Hepatobiliary failure | 0.65 | 0.03 |
| Acute renal failure | 0.81 | 0.22 |
| Cerebral dysfunction | 0.20 | 0.02 |
| DIC | 0.54 | 0.002 |
| Shock | 0.97 | 0.04 |

SMART was also applied to selected patient parameters collected at pre-randomization baselinbe in two sequential clinical trials, NORASEPT I and NORASEPT II, that tested the efficacy of an antibody against tumor necrosis factor (TNFMab) in patients with severe sepsis and septic shock. SMART profiles were generated from the NORASEPT I database using the following selected patient parameters: APACH Score, demographics information, vitals at infusion, laboratory results from blood and urine analysis, hematology laboratory results, pulmonary assessment, sepsis, shock episodes, and organ failure. Logistical regressions of the SMART profiles for predicting mortality in patients receiving placebo and patients receiving treatment in the NORASEPT I study are depicted below:

Patients Receiving Placebo/Outcome is Death on or Before 30 Days

| Parameter | DF | Estimate | Standard Error | Chi-Square | Pr > ChiSq |
|---|---|---|---|---|---|
| Intercept | 1 | −1.8724 | 0.8723 | 4.6077 | 0.0318 |
| APACHE | 1 | 0.0796 | 0.0213 | 13.9415 | 0.0002 |
| B1_Urinary_Tract | 1 | −0.9126 | 0.3031 | 9.0637 | 0.0026 |
| Respiratory | 1 | 0.7521 | 0.4260 | 3.1169 | 0.0775 |
| RESP | 1 | 0.0383 | 0.0154 | 6.1520 | 0.0131 |
| DIAST | 1 | −0.0315 | 0.00939 | 11.2441 | 0.0008 |
| DIC | 1 | 2.0274 | 0.4054 | 25.0156 | <.0001 |

Odds Ratio Estimate

| Effect | Point Estimate | 95% Wald Confidence Limits | |
|---|---|---|---|
| APACHE | 1.083 | 1.039 | 1.129 |
| B1_Urinary_Tract | 0.0401 | 0.222 | 0.727 |
| Respiratory | 2.121 | 0.920 | 4.889 |
| RESP | 1.039 | 1.008 | 1.071 |
| DIAST | 0.969 | 0.951 | 0.987 |
| DIC | 7.594 | 3.431 | 16.808 |

Patients Receiving Treatment/Outcome is Death on or Before 30 Days

| Parameter | DF | Estimate | Standard Error | Chi-Square | Pr > ChiSq |
|---|---|---|---|---|---|
| Intercept | 1 | −6.2303 | 0.7692 | 65.6038 | <.0001 |
| APACHE | 1 | 0.0920 | 0.0217 | 18.0320 | <.0001 |
| AGE | 1 | 0.0457 | 0.00958 | 22.7774 | <.0001 |
| Neurologic | 1 | 0.9696 | 0.3450 | 7.8958 | 0.0050 |
| CNSD | 1 | −1.3140 | 0.3337 | 15.5021 | <.0001 |
| ARDS | 1 | 2.1080 | 0.4077 | 26.7285 | <.0001 |
| DIC | 1 | 1.2307 | 0.4772 | 6.6513 | 0.0099 |
| HBD | 1 | 1.7484 | 0.6112 | 8.1821 | 0.0042 |

Odds Ratio Estimate

| Effect | Point Estimate | 95% Wald Confidence Limits | |
|---|---|---|---|
| APACHE | 1.096 | 1.051 | 1.144 |
| AGE | 1.047 | 1.027 | 1.067 |
| Neurologic | 2.637 | 1.341 | 5.185 |
| CNSD | 0.269 | 0.140 | 0.517 |
| ARDS | 8.232 | 3.702 | 18.304 |
| DIC | 3.424 | 1.344 | 8.724 |
| HBD | 5.745 | 1.734 | 10.037 |

Baseline data of selected patient parameters from the NORASEPT II patients was then entered into the SMART profiles generated from the NORASEPT I study and the predictiveness of the SMART profiles in determining efficacy of the TNFmAb in patients with sepsis or septic shock was assessed. Survival analyses in all patients versus SMART patients are depicted below:

All Subjects:

Summary of the Number of Censored and Uncensored Values

| DRUG | Total | Failed | Censored | % Censored |
|---|---|---|---|---|
| Placebo | 863 | 379 | 484 | 56.0834 |
| TNFMab | 878 | 360 | 518 | 58.9977 |
| Total | 1741 | 739 | 1002 | 57.5531 |

| TEST | Chi-Square | DF | p-value |
|---|---|---|---|
| −2logLR | 2.0472 | 1 | 0.1525 |

SMART SUBJECTS: Treatment death probability le 0.6 and Placebo Death Probability ge 0.3

| DRUG | Total | Failed | Censored | % Censored |
|---|---|---|---|---|
| Placebo | 371 | 184 | 187 | 50.4043 |
| TNFMab | 373 | 158 | 215 | 57.6408 |
| Total | 744 | 342 | 402 | 54.0323 |

| TEST | Chi-Square | DF | p-value |
|---|---|---|---|
| −2LogLR | 5.3601 | 1 | 0.0206 |

Thus, as shown herein, SMART can identify objectively at pre-randomization baseline individual patients who are biologically appropriate for a study drug. These predictions can supplement clinical entry criteria for studies of antibiotics, cancer treatments, and transplant regimens, among others, as well as new drugs for sepsis, acute organ failure, and other systemic inflammatory conditions. SMART profiles ensure that the study drug receives a reasonable chance to demonstrate its efficacy in the conditions under treatment. After SMART profiling is used to demonstrate a drug's efficacy, SMART profiles can then be applied at the bedside to identify individual patients for whom the drug in question is beneficial. Using SMART, the host inflammatory response of individuals can now be matched to the biopharmacologic properties of a drug.

The invention is further illustrated by the following nonlimiting examples.

EXAMPLES

Example 1

Measurement of Plasma Levels of the Leukotrienes, Prostaglandins, Cytokines, Platelet Activating Factor and Neutrophil Elastase Plasma levels of leukotrienes B4, C4, D4 and E4, TxB, PGI, TNF-α, interleukin-1β, interleukin-6, neutrophil elastase and platelet activating factor are measured using ELISA immunoassay techniques. A blood sample from a patient is collected in a sterile polypropylene tube containing EDTA, indomethacin, and ketoconazole and spun immediately at 1500 g for 10 minutes at 4° C. The supernatant is pipetted into individual aliquots for each assay and stored at −70° C. until the assay is performed. Sandwich and single antibody ELISA assays specific for each compound are performed using commercially available ELISA kits. Standard curve and known spiked standards in the mid-range of the detectable limit for each compound are included on each ELISA plate. Percent recovery and intra- and inter-assay coefficients of variation are calculated to ensure quality control of each assay.

Example 2

Radioimmunoassay of Complement Components C3a and C5a

Plasma levels of complement components C3a des arg and C5a des arg are measured by radioimmunoassay. Blood samples are collected from patients and prepared as described in Example 1. Radioimmunoassay of C3a and C5a are then performed with commercially available standards, trace compounds and antisera according to standard radioimmunoassay procedures. Percent recovery and intra-assay variation coefficients of variation are calculated to ensure quality control of each assay.

Example 3

Quantification of Nitric Oxide

Plasma concentration of nitric oxide are analyzed quantitatively by measurement of nitrate and nitrite, the stable in-products of nitric oxide metabolism, as an index of nitric oxide synthesis. Blood samples are obtained and processed as described in Example 1. The resulting plasma is deproteinized with 0.5 M NaOH and 10% $ZnSO_4$. Plasma nitrite/nitrate levels are determined using an automated procedure based on the Greiss reaction (Green L C, et al., *Anal Biochem* 126:131-138, 1982). Levels can also be determined by ELISA (as total nitrite) in accordance with techniques which are well known in the art.

Example 4

Measurement of Plasma Endotoxin

Levels of endotoxin in plasma sample are measured by the triple metric modification of the *Limulus amebocyte* lysate assay for endotoxin. Blood sample are collected and processed as described in Example 1. Quantitative endotoxin measurements are performed with commercially available standards in Limulus lysate assay reagent (Associates of Cape Cod, Woods Hole, Mass.).

Example 5

Platelet Aggregometry

Measurement of platelet aggregometry is performed using an automatic dual channel platelet aggregometer with platelet rich plasma prepared by standard laboratory techniques. Blood samples collected from patients are anticoagulated with EDTA, indomethacin and ketoconazole and immediately spun at 100 rpm for 10 minutes. The resultant platelet-rich plasma is removed. The remaining samples are then spun at 3,000 rpm for 30 minutes to obtain platelet-poor plasma. The number of platelets in the platelet-rich plasma is determined. The platelet-rich plasma is then adjusted to approximately 250,000 to 300,000 platelets per ml of plasma with autologous platelet-poor plasma from the same patient to form a platelet suspension. After adjustment 0.45 ml of the platelet suspension is transferred to a siliconized cuvette containing a siliconized stirring bar and allowed to warm for two minutes to 37° C. After warming, 1 μM ADP in 0.05 ml Hank's balanced salt solution is added and the resulting changes in light transmission are recorded. Changes in light transmission after the addition of 1 μM ADP to platelet-rich plasma from control samples prepared from blood of normal volunteer donors are compared to those produced with plasma from patients and expressed as the percentage of the maximum light transmission response of control samples to 1 μM ADP.

Example 6

Granulocyte Aggregometry

Measurement of granulocyte aggregation is performed using an automatic dual channel platelet aggregometer with granulocyte-rich plasma. Granulocyte-rich plasma is prepared in accordance with standard laboratory techniques described by Craddock et al., *J Clin Invest* 60:260-264, 1977, and modified by Hammerchmidt et al., *Blood* 55(6): 898-902, 1980. Blood samples from patients are collected in pyrogen-free polypropylene tubes containing EDTA, indomethacin and ketoconazole. The samples are spun at 1500 g for 10 minutes at 4° C. and the supernatant fraction pipetted off. Granulocyte suspension are prepared from blood of normal volunteer donors. Blood is withdrawn into a syringe containing EDTA, indomethacin and ketoconazole. The blood samples are then diluted with buffered saline, pH 7.4, layered over a 1.075/1.10 density Percoll gradient (Pharmacia Inc. Piscataway, N.J.), and spun at 400 g for 45 minutes. The supernatant is discarded. The cell button is resuspended in 0.83% $NH_4Cl$, incubated at 37° C. for 6 minutes and spun at 400 g for 5 minutes. This procedure to the cell button is then repeated. Following the second centrifugation, the cell button is washed three times with phosphate buffered saline, spun against at 400 g for 5 minutes and the supernatant discarded. The cell button is then resuspended in Hank's balanced salt solution with 0.5% bovine serum albumin. The cell suspension is counted and diluted to obtain a final concentration of 1 to $1.5 \times 10^7$ cells per ml. A 0.45 ml aliquot of the cell suspension is added to a siliconized cuvette containing a siliconized stirring bar in a platelet aggregometer and allowed to warm for two minutes to 37° C. After warming, 0.05 ml of plasma from a patient is added to the cuvette and the resulting changes in light transmission are recorded. Changes in light transmission following addition of plasma from a patient are compared to those changes produced using the same cell suspension stimulated by control plasma activated with zymosan. Preparation of zymosan-activated plasma (ZAP) is described in Example 7, infra. Values are expressed as a percent of the maximum light transmission recorded after addition of ZAP.

Example 7

Preparation of Zymosan-Activated Plasma (ZAP)

Blood from normal volunteer donors is drawn into heparinized syringes and centrifuged at 2800 rpm for 10 minutes to separate the plasma fraction. Zymosan solution (20 mg/ml) is added to the plasma to a concentration of 2.0 mg/ml. The plasma is then incubated at 37° C. for 30 minutes with tumbling. The suspension is then cooled to 4° C. and spun at 2800 rpm for 10 minutes. The ZAP is removed and the zymosan button discarded.

Example 8

Measured Physiologic Parameters from Patients with Sepsis

Physiologic parameters in nine septic patients were monitored for 4 days. Each of these patients suffered from most, if not all, of the following: a fever greater than 100.4° F.; a heart rate greater than 90 beats/minute; a respiratory rate greater than 20 breaths/minute or mechanical ventilation required; other clinical evidence to support a diagnosis of sepsis syndrome; profound systemic hypotension characterized by a systolic blood pressure of less than 90 mm mercury or a mean arterial pressure less than 70 mm mercury; clinical dysfunction of the brain, lungs, liver, or coagulation system; a hyperdynamic cardiac index and systemic vascular resistance, and systemic metabolic/lactic acidosis. Levels of thromboxane B2, prostaglandin 6-keto F1α (PGI), leukotrienes $B_4$, $C_4$, $D_4$ and $E_4$, interleukin-1, tumor necrosis factor α, and interleukin-6 were measured serially in plasma from these patients. Leukotriene $B_4$ and/or tumor necrosis factor α were detectable in only two patients. Plasma levels of thromboxane $B_2$, PGI, and the complements of leukotrienes $C_4$, $D_4$ and $E_4$ were elevated above normal and increased significantly from baseline during the first 72 hours. Plasma levels of interleukin-1β did not change from baseline, however, levels of interleukin-6 rose sequentially to 118% of the baseline values. In 10 additional patients who received a 72 hour infusion of human recombinant interleukin-1 antagonist, at 72 hours thromboxane $B_2$, PGI, leukotrienes $C_4$, $D_4$ and $E_4$, and interleukin-6 plasma levels were significantly lower. Interleukin-1β was significantly increased in these patients when compared with septic patients who received only standard care. Retrospective data analysis of the overall study suggested survival benefit in patients who received the interleukin-1 antagonist which, in the sub-group studied above, had lower prostaglandin, leukotriene, and IL-6 levels and higher plasma interleukin-1.

Example 9

Application of the SMART Profile to Patients Enrolled in a Clinical Trial for Severe Sepsis The purpose of this study was to demonstrate the ability of the SMART method to identify interactions among physiologic parameters, standard hospital laboratory tests, patient demographics, and circulating cytokine levels that predict continuous and dichotomous dependent clinical variables in advance in individual patients with severe sepsis and septic shock. Patients (n=303) with severe sepsis or septic shock were entered into the placebo arm of a multi-institutional clinical trial. The patients were randomly divided into a model-building training cohort (n=200) and a prospective validation or predictive cohort (n=103). Demographics, including sex, race, age, admitting service (surgery or non-surgical), and co-morbidities were recorded at baseline for each patient. At baseline and on days 1 through 7, 14, 21, and 28, the physiologic parameters and hospital laboratory tests listed on Table 1 were recorded. In addition, at baseline and on days 1, 2, 3, and 4 plasma concentrations of interleukin-6 (IL-6), interleukin-8 (IL-8), and granulocyte colony stimulating factor (GCSF) were measured by ELISA using commercially available kits and standard ELISA methodology.

The continuous dependent variables were screened for cross-correlations with each independent variable at days 1-7, 14, 21, and 28 after baseline. Cross correlations with correlation coefficients of 0.1 or higher were then entered into a matrix program in which multiple regression models with all ways elimination were built for each continuous dependent variable for each day. In order to maintain adequate standards for statistical power, the number of independent variables included in each model was limited to approximately one for every 20 patients in each data set evaluated. These multiple regression predictive models then were validated prospectively by entering raw data from each of the patients in the predictive cohort into them and plotting linear regression curves for the predictive value of each variable for each patient versus the measurements actually observed. The extent of agreement between the quantitative predictions and observed data then was described by the Pearson product moment or linear regression correlation coefficient.

Again using the training cohort, multivariate models that predicted the presence or absence of the clinical entities such as ARDS, renal insufficiency, DIC, according to established diagnostic criteria in the literature for these entities, as well as cerebral dysfunction (Glasgow Coma Scale less than 11), and the number of lung quadrants on chest x-ray that were affected by pulmonary edema (0-4) were developed through a step-wise logistic regression. Glasgow Coma Scale less than 11 was chosen as a threshold for cerebral dysfunction because of the automatic absence of an appropriate verbal response for endotracheally intubated patients whom otherwise have intact cerebral function. The SMART multiple regression models derived for these dichotomous dependent variables were then validated prospectively by entering raw data from individual patients in the predictive cohort into the training cohort logistic regression formulae, and then assessing predictive accuracy by calculating the area under the curve (AUC) of receiver operator characteristic statistics. Multiple regression and stepwise multivariate logistic models that predicted continuous and dichotomous dependent variables, respectively, 24 hours after baseline, used baseline data only. For predictions beyond 24 hours, SMART modeling was carried out in two ways for each variable at each measured time point: 1) from baseline data only; 2) from serial data where baseline measurements and/or subsequent determinations up to 24 hours before the time being prognosticated were incorporated into the multiple regression and/or multivariate stepwise logistic regression modeling. The differences between baseline and serial predictive models were evaluated statistically using Fisher's z transformation. For this study, statistical significance was established at the 95% confidence interval with a z-statistic greater than or equal to 1.96.

Prospectively validated SMART predictions of physiologic, respiratory, and metabolic parameters in patients with severe sepsis and septic shock, resulting from multivariate models derived from baseline data only are listed in Table 2. The highest linear regression correlation coefficients were seen for predictions of the level of pressure support ventilation, PEEP, serum albumin, cholesterol, total protein, triglycerides, and uric acid. Through 7 days, quantitative predictions of $HCO_3$, $FiO_2$, SVR, cardiac index, temperature, and heart rate also approached clinically useful levels of prospective validation. Predictions from baseline data of continuous dependent variables at 14 days and beyond were consistently significant only for $HCO_3$, serum albumin, cholesterol, total protein, uric acid, and calcium.

Results of prospectively validated SMART multiple regression predictions of liver and renal function indicators among patients with severe sepsis from baseline data only are shown in Table 3. Clinically useful levels of correlation between SMART predictions and the values actually observed in individual patients were achieved for alkaline phosphatase, alanine aminotransferase (ALT), aspartate aminotransferase (AST), glutamyl-glutamate aminotransferase (GGT), total bilirubin, BUN, and creatinine. Many of the multiple regression models yielded clinically useful results at 14 days and beyond.

Prospectively validated SMART predictions of hematologic and coagulation indicators in patients with severe sepsis from baseline data only are tabulated in Table 4. Quantitative prediction from baseline data for lymphocyte, monocyte, segmental neutrophil, band, and granulocyte counts, and differential percentage of granulocytes and lymphocytes, platelet count, and prothrombin time (PT) consistently resulted in linear regression correlations between predicted and observed values in individual patients in the clinically useful range above 0.9. SMART predictions of hematocrit, red blood cell count (RBC), and white blood cell count (WBC), and PTT (partial thromboplastin time) also were significant.

Prospectively validated SMART predictions of physiologic, respiratory, and metabolic parameters in patients with severe sepsis from baseline data plus serial information, including maximum levels and change from baseline are tabulated in Table 5. Plots of predicted versus observed values in individual patients for Glasgow Coma Scale, $HCO_3$, pressure support ventilation, PEEP, albumin, cholesterol, triglycerides, and uric acid produced r values greater than 0.8 during days 1-7. Predicted versus observed correlations above 0.4 were recorded for heart rate, temperature, cardiac index, SVR, $FiO_2$, glucose, total protein, and calcium.

Prospective validated SMART predictions of liver and renal function indicators from baseline plus serial data are shown in Table 6. Clinically useful levels of accuracy, evidenced in Pearson product moments exceeding 0.8 were achieved with alkaline phosphatase, ALT, GGT, total bilirubin, BUN, and creatinine for up to 28 days of observation.

Prospective validated SMART predictions of hematologic and coagulation indicators in patients with severe sepsis from models derived from baseline plus serial data analysis are shown in Table 7. Clinically useful levels of accuracy were evidenced in r values exceeding 0.9 for SMART predictions of lymphocyte, monocytes, segmental neutrophil, band, and granulocyte counts, differential percentage of granulocytes and lymphocytes, platelet count, and prothrombin time. Pearson product moments exceeding 0.5 were recorded also for hematocrit, RBC, WBC, and PTT.

Predicted versus observed linear regression coefficients for continuous dependent variables in patients with severe sepsis are tabulated in Table 8. Through day 3, over half of the predicted versus observed plots of individual patients had r values at or above 0.7. For days 4 and 5, most multiple regression models were validated at or above the 0.5 level. Among predictions beyond 14 days, approximately 20% of r values were at or above 0.6. Clinically useful levels of accuracy, reflected by Pearson product moments greater than 0.8 were noted in 50% of SMART predictions for continuous dependent variables at day 1, 47% at day 2, and 25% at day 3. Thereafter, through day 28, 14 to 22% of quantitative predictions in individual patients generated predicted versus observed plots at or above the 0.8 r value level of accuracy.

The distribution of regression coefficients for prospectively validated SMART predictions of continuous dependent variables in individual patients with severe sepsis from baseline data plus serial data are listed in Table 9. Through day 5, from baseline, over half of predicted versus observed r values were greater than 0.5, and 53% had r values exceeding 0.8 at day 3 from baseline. On days 4-28, between 17% and 31% of serial data multiple regression models generated predictive versus observed Pearson product moments of 0.8 and higher.

In order to determine the ability of the SMART predictive modeling process to predict organ failure and shock subclinically in patients with severe sepsis, baseline data from patients in the predictive cohort who did not have ARDS at baseline were entered into the SMART models for predicting ARDS from baseline data on days 1-28. Similarly, data from patients who did not have DIC at baseline were entered into models for DIC and so on, as well as for individual patients who did not have hepatobiliary failure, renal insufficiency, shock, and Glasgow Coma Scale less than 11 at baseline. SMART multiple logistic regression models predicted the presence or absence of ARDS, DIC, hepatobiliary failure, renal insufficiency, shock, and cerebral dysfunction in patients without each of these conditions at baseline up to 28 days in advance with 25 of 60 (42%) achieving ROC AUC values of 0.7 and higher. Conversely, predicted versus observed analysis for shock and each type of organ dysfunction was performed using baseline data from predictive cohort patients who did have shock or organ dysfunction at baseline. In 38 of 60 models (63%), the ROC AUC for predicted versus observed plots exceeded 0.5, thus predicting the continued presence or resolution of shock and organ failure.

TABLE 1

Independent Variables in Patients with Severe Sepsis

| | | |
|---|---|---|
| Age | WBL | $PaO_2/FiO_2$ |
| Sex | IL-6 | Chloride |
| Race | IL-8 | Eosinophils |
| Albumin | GCSF | Lymphocytes |
| Alkaline phosphatase | EKG: P-r and q-T intervals | Segmental neutrophils |
| ALT | DIC | Metamyelocyte |

TABLE 1-continued

Independent Variables in Patients with Severe Sepsis

| | | |
|---|---|---|
| AST | GCS | Mononuclear cells |
| BUN | Hepatobiliary failure | Band neutrophil |
| Calcium | Shock | Basophils |
| Cholesterol | ARDS | Granulocytes |
| Creatinine | Renal failure | % Granulocytes |
| GGT | Coma | % Lymphocytes |
| Glucose | Alcohol abuse/cirrhosis | Eosinophils |
| Hematocrit | HIV | Lactic acid |
| MCH | Dialysis | PCWP |
| MCHC | Neutropenia | Cardiac index |
| MCV | COPD | SVR |
| Phosphorus | Solid tumor | PEEP |
| Platelet count | Hematologic malignancy | Pressure support |
| Potassium | Chronic renal failure | Respiratory rate |
| Total protein | Mechanical ventilation | Admitting service |
| PT | $AaDO_2$ | Trauma |
| PTT | Base deficit | Systolic BP |
| RBL | pH | Diastolic BP |
| Sodium | $PaO_2$ | Heart rate |
| Total bilirubin | $SaO_2$ | MAP |
| Triglycerides | $FiO_2$ | Temperature |
| Uric acid | Fluids in/out | Height/Weight |

TABLE 2

Prediction of Physiologic, Respiratory and Metabolic Parameters from Baseline Data Only

| | Day | | | | | | | | | |
|---|---|---|---|---|---|---|---|---|---|---|
| $r^1$ | 1 | 2 | 3 | 4 | 5 | 6 | 7 | 14 | 21 | 28 |
| Heart Rate | 0.429 | 0.425 | 0.310 | 0.249 | 0.360 | 0.386 | 0.377 | 0.109 | 0.183 | 0.366 |
| Temperature | 0.468 | 0.411 | 0.161 | 0.243 | 0.371 | 0.295 | 0.342 | 0.033 | 0.177 | — |
| Cardiac Index | 0.570 | 0.445 | 0.645 | 0.437 | 0.525 | 0.440 | — | — | — | — |
| SVR | 0.488 | 0.304 | 0.420 | −.014 | 0.061 | 0.265 | 0.124 | — | — | — |
| Glasgow Coma Scale | 0.601 | 0.575 | 0.458 | 0.387 | 0.287 | 0.400 | 0.325 | 0.184 | 0.213 | 0.101 |
| $FiO_2$ | 0.443 | 0.115 | 0.078 | 0.452 | 0.517 | 0.308 | 0.409 | 0.023 | 0.218 | 0.092 |
| $HCO_3$ | 0.571 | 0.551 | 0.562 | 0.477 | 0.500 | 0.401 | 0.350 | 0.371 | 0.421 | 0.126 |
| Pressure Support | 0.893 | 0.738 | 0.763 | 0.402 | 0.421 | 0.481 | 0.167 | — | 0.290 | — |
| PEEP | 0.893 | 0.716 | 0.669 | 0.372 | 0.391 | 0.270 | 0.317 | 0.168 | 0.016 | 0.071 |
| Albumin | 0.881 | 0.720 | 0.770 | 0.767 | 0.767 | 0.709 | 0.647 | 0.420 | 0.373 | 0.204 |
| Cholesterol | 0.725 | 0.832 | 0.794 | 0.722 | 0.479 | 0.395 | 0.295 | 0.356 | 0.258 | 0.055 |
| Glucose | 0.217 | 0.251 | 0.247 | 0.447 | 0.472 | — | 0.079 | 0.197 | 0.239 | 0.313 |
| Total Protein | 0.785 | 0.684 | 0.701 | 0.635 | 0.587 | 0.556 | 0.483 | 0.289 | 0.229 | 0.031 |
| Triglycerides | 0.711 | 0.922 | 0.771 | 0.403 | 0.407 | 0.313 | 0.155 | 0.343 | 0.194 | 0.120 |
| Uric Acid | 0.939 | 0.910 | 0.826 | 0.740 | 0.685 | 0.593 | 0.506 | 0.283 | 0.353 | 0.512 |
| Calcium | 0.696 | 0.663 | 0.424 | 0.580 | 0.611 | 0.605 | 0.510 | 0.360 | 0.450 | 0.312 |

TABLE 3

Prediction of Liver and Renal Function Indicators in Severe Sepsis From Baseline Data Only

| $r^1$ | Day | | | | | | | | | |
|---|---|---|---|---|---|---|---|---|---|---|
| | 1 | 2 | 3 | 4 | 5 | 6 | 7 | 14 | 21 | 28 |
| Alkaline Phosphatase | 0.869 | 0.550 | 0.691 | 0.679 | 0.798 | 0.710 | 0.619 | 0.421 | 0.369 | 0.105 |
| ALT | 0.959 | 0.844 | 0.391 | 0.485 | 0.606 | 0.242 | 0.224 | 0.354 | 0.305 | 0.108 |
| AST | 0.786 | 0.659 | 0.231 | 0.287 | 0.153 | 0.061 | 0.093 | — | — | 0.461 |
| GGT | 0.943 | 0.807 | 0.717 | 0.707 | 0.671 | 0.499 | 0.578 | 0.491 | 0.456 | 0.169 |
| Total Bilirubin | 0.965 | 0.941 | 0.832 | 0.676 | 0.770 | 0.753 | 0.824 | 0.869 | 0.815 | 0.688 |
| BUN | 0.970 | 0.922 | 0.881 | 0.832 | 0.816 | 0.804 | 0.767 | 0.450 | 0.337 | 0.331 |
| Creatinine | 0.896 | 0.831 | 0.741 | 0.706 | 0.657 | 0.645 | 0.567 | 0.303 | 0.384 | 0.379 |

TABLE 4

Prediction of Hematologic and Coagulation Indicators In Severe Sepsis From Baseline Data

| $r^1$ | Day | | | | | | | | | |
|---|---|---|---|---|---|---|---|---|---|---|
| | 1 | 2 | 3 | 4 | 5 | 6 | 7 | 14 | 21 | 28 |
| Hematocrit | 0.512 | 0.226 | 0.297 | 0.332 | 0.514 | 0.391 | 0.378 | 0.220 | 0.417 | 0.044 |
| RBC | 0.592 | 0.371 | 0.288 | 0.310 | 0.447 | 0.354 | 0.384 | 0.075 | 0.323 | 0.119 |
| WBC | 0.726 | 0.481 | 0.259 | 0.304 | 0.041 | 0.236 | 0.317 | 0.476 | 0.242 | 0.231 |
| Lymphocytes | 0.937 | 0.982 | 0.976 | 0.994 | 0.105 | 0.158 | 0.114 | 0.995 | 0.978 | 0.980 |
| Monocytes | 0.971 | 0.998 | 0.997 | 0.994 | 0.999 | 0.161 | 0.168 | 0.988 | 0.999 | 0.997 |
| Segmental Neutrophils | 0.999 | 0.999 | 0.999 | 0.999 | 0.999 | 0.999 | 0.999 | 0.989 | 0.995 | 0.999 |
| Bands | 0.999 | 0.991 | 0.704 | 0.511 | 0.935 | 0.994 | 0.984 | 0.020 | 0.102 | 0.331 |
| Granulocytes | 0.999 | 0.999 | 0.999 | 0.859 | 0.999 | 0.878 | 0.734 | 0.637 | 0.999 | — |
| % Granulocytes | 0.999 | 0.999 | 0.999 | 0.685 | 0.999 | 0.999 | 0.999 | 0.245 | 0.999 | — |
| % Lymphocytes | 0.116 | 0.985 | 0.977 | 0.158 | 0.100 | 0.184 | — | 0.959 | 0.979 | 0.973 |
| Platelet Count | 0.921 | 0.850 | 0.777 | 0.732 | 0.670 | 0.604 | 0.438 | 0.301 | 0.450 | 0.147 |
| PT | 0.932 | 0.923 | 0.926 | 0.922 | 0.917 | 0.402 | 0.928 | 0.879 | 0.809 | 0.887 |
| PTT | 0.482 | 0.474 | 0.483 | 0.462 | 0.232 | 0.377 | 0.215 | 0.255 | 0.169 | 0.042 |

TABLE 5

Prediction of Physiologic, Respiratory and Metabolic Parameters In Severe Sepsis From Serial Data

| $r^1$ | Day | | | | | | | | | |
|---|---|---|---|---|---|---|---|---|---|---|
| | 1 | 2 | 3 | 4 | 5 | 6 | 7 | 14 | 21 | 28 |
| Heart Rate | 0.429 | 0.424 | 0.440 | 0.123 | 0.390 | 0.364 | 0.275 | 0.111 | 0.231 | 0.353 |
| Temperature | 0.468 | 0.422 | 0.205 | 0.233 | 0.354 | 0.230 | 0.300 | 0.231 | 0.201 | 0.031 |
| Cardiac Index | 0.570 | 0.157 | 0.404 | 0.352 | 0.298 | 0.167 | 0.007 | — | — | — |
| SVR | 0.488 | 0.065 | 0.224 | 0.700 | 0.804 | 0.328 | 0.223 | — | — | — |
| Glasgow Coma Scale | 0.601 | 0.897 | 0.804 | 0.665 | 0.377 | 0.024 | 0.164 | — | 0.066 | 0.079 |
| $FiO_2$ | 0.443 | 0.120 | 0.078 | 0.419 | 0.336 | 0.310 | 0.382 | 0.455 | 0.137 | 0.057 |
| $HCO_3$ | 0.571 | 0.277 | 0.853 | 0.375 | 0.362 | 0.211 | 0.350 | 0.112 | 0.233 | 0.218 |
| Pressure Support | 0.893 | 0.877 | 0.904 | 0.674 | 0.620 | 0.481 | 0.297 | 0.258 | — | 0.325 |
| PEEP | 0.892 | 0.877 | 0.899 | 0.674 | 0.263 | 0.291 | 0.450 | 0.167 | 0.368 | 0.188 |
| Albumin | 0.881 | 0.815 | 0.937 | 0.794 | 0.819 | 0.680 | 0.622 | 0.386 | 0.227 | 0.055 |
| Cholesterol | 0.725 | 0.832 | 0.957 | 0.633 | 0.403 | 0.303 | 0.180 | 0.287 | 0.011 | 0.058 |
| Glucose | 0.217 | 0.225 | 0.407 | 0.478 | 0.437 | 0.133 | 0.024 | 0.192 | 0.223 | 0.120 |
| Total Protein | 0.785 | 0.656 | 0.638 | 0.598 | 0.588 | 0.563 | 0.520 | 0.324 | 0.047 | 0.204 |
| Triglycerides | 0.711 | 0.846 | 0.802 | 0.415 | 0.602 | 0.454 | 0.158 | 0.457 | 0.384 | 0.117 |
| Uric Acid | 0.939 | 0.910 | 0.957 | 0.720 | 0.623 | 0.545 | 0.446 | 0.304 | 0.353 | 0.517 |
| Calcium | 0.696 | 0.522 | 0.346 | 0.589 | 0.551 | 0.635 | 0.142 | 0.357 | 0.553 | 0.153 |

TABLE 6

Prediction of Liver and Renal Function Indicators in Severe Sepsis From Serial Data

| | Day | | | | | | | | | |
|---|---|---|---|---|---|---|---|---|---|---|
| $r^1$ | 1 | 2 | 3 | 4 | 5 | 6 | 7 | 14 | 21 | 28 |
| Alkaline Phosphatase | 0.869 | 0.594 | 0.689 | 0.055 | 0.878 | 0.720 | 0.809 | 0.699 | 0.670 | 0.818 |
| ALT | 0.959 | 0.865 | 0.772 | 0.506 | 0.497 | 0.175 | 0.016 | 0.041 | 0.161 | 0.572 |
| AST | 0.786 | 0.659 | 0.605 | 0.180 | 0.134 | 0.302 | — | — | 0.138 | 0.426 |
| GGT | 0.943 | 0.810 | 0.837 | 0.689 | 0.701 | 0.683 | 0.736 | 0.652 | 0.443 | 0.415 |
| Total Bilirubin | 0.965 | 0.982 | 0.983 | 0.889 | 0.895 | 0.912 | 0.822 | 0.927 | 0.949 | 0.933 |
| BUN | 0.970 | 0.970 | 0.946 | 0.906 | 0.811 | 0.844 | 0.792 | 0.419 | 0.553 | 0.429 |
| Creatinine | 0.896 | 0.879 | 0.815 | 0.716 | 0.603 | 0.593 | 0.568 | 0.312 | 0.384 | 0.359 |

TABLE 7

Prediction of Hematologic and Coagulation Indicators In Severe Sepsis From Serial Data

| | Day | | | | | | | | | |
|---|---|---|---|---|---|---|---|---|---|---|
| $r^1$ | 1 | 2 | 3 | 4 | 5 | 6 | 7 | 14 | 21 | 28 |
| Hematocrit | 0.512 | 0.400 | 0.045 | 0.560 | 0.410 | 0.450 | 0.403 | 0.181 | 0.027 | 0.025 |
| RBC | 0.592 | 0.658 | 0.691 | 0.134 | 0.330 | 0.369 | 0.382 | — | 0.179 | 0.327 |
| WBC | 0.726 | 0.481 | 0.751 | 0.426 | 0.095 | 0.357 | 0.353 | 0.516 | 0.377 | 0.116 |
| Lymphocytes | 0.937 | 0.982 | 0.975 | 0.989 | 0.132 | 0.996 | 0.970 | 0.994 | 0.986 | 0.981 |
| Monocytes | 0.971 | 0.989 | 0.989 | 0.387 | 0.999 | 0.161 | 0.139 | 0.988 | 0.999 | 0.998 |
| Segmental Neutrophils | 0.999 | 0.999 | 0.999 | 0.999 | 0.999 | 0.999 | 0.999 | 0.999 | 0.999 | 0.999 |
| Bands | 0.999 | 0.989 | 0.038 | 0.519 | 0.956 | 0.995 | 0.980 | 0.095 | 0.102 | 0.386 |
| Granulocytes | 0.999 | 0.999 | 0.999 | 0.857 | 0.999 | 0.999 | 0.748 | 0.658 | 0.999 | — |
| % Granulocytes | 0.999 | 0.999 | 0.999 | 0.704 | 0.999 | 0.999 | 0.999 | 0.209 | 0.999 | — |
| % Lymphocytes | 0.116 | 0.974 | 0.986 | 0.969 | 0.116 | 0.996 | — | 0.963 | 0.984 | 0.977 |
| Platelet Count | 0.921 | 0.894 | 0.759 | 0.754 | 0.754 | 0.789 | 0.726 | 0.382 | 0.743 | 0.581 |
| PT | 0.932 | 0.932 | 0.991 | 0.885 | 0.912 | 0.911 | 0.900 | 0.866 | 0.849 | 0.865 |
| PTT | 0.482 | 0.507 | 0.472 | 0.434 | 0.246 | 0.279 | 0.348 | 0.181 | 0.726 | — |

TABLE 8

Predicted vs. Observed Linear regression Coefficients for Continuous Dependent Variables In Patients with Severe Sepsis From Baseline Data

| Days After Baseline | Regression Coefficient | | | | |
|---|---|---|---|---|---|
| | >0.5 | >0.6 | >0.7 | >0.8 | >0.9 |
| 1 | 29/36 (81%) | 25/36 (69%) | 22/36 (61%) | 18/36 (50%) | 13/36 (36%) |
| 2 | 26/36 (72%) | 23/36 (64%) | 20/36 (56%) | 9/36 (25%) | 7/36 (19%) |
| 3 | 22/36 (61%) | 22/36 (61%) | 19/36 (53%) | 9/36 (25%) | 7/36 (19%) |
| 4 | 18/36 (50%) | 16/36 (44%) | 12/36 (33%) | 6/36 (19%) | 4/36 (11%) |
| 5 | 21/36 (58%) | 16/36 (44%) | 10/36 (28%) | 7/36 (19%) | 6/36 (17%) |
| 6 | 13/36 (36%) | 11/36 (31%) | 8/36 (22%) | 5/36 (14%) | 3/36 (8%) |
| 7 | 13/36 (36%) | 9/36 (25%) | 7/36 (19%) | 5/36 (14%) | 4/36 (11%) |
| 14 | 7/36 (19%) | 7/36 (19%) | 6/36 (17%) | 6/36 (17%) | 4/36 (11%) |
| 21 | 8/36 (22%) | 8/36 (22%) | 8/36 (22%) | 8/36 (22%) | 6/36 (17%) |
| 28 | 6/36 (17%) | 6/36 (17%) | 5/36 (14%) | 5/36 (14%) | 4/36 (11%) |

TABLE 9

Predicted vs. Observed Linear regression Coefficients for Continuous Dependent Variables In Patients with Severe Sepsis From Serial Data

| Days After Baseline | Regression Coefficient | | | | |
|---|---|---|---|---|---|
| | >0.5 | >0.6 | >0.7 | >0.8 | >0.9 |
| 1 | 29/36 (81%) | 25/36 (69%) | 22/36 (61%) | 18/36 (50%) | 13/36 (36%) |
| 2 | 26/36 (72%) | 23/36 (64%) | 21/36 (58%) | 21/36 (58%) | 13/36 (36%) |
| 3 | 26/36 (72%) | 26/36 (72%) | 21/36 (58%) | 19/36 (53%) | 13/36 (36%) |
| 4 | 22/36 (61%) | 13/36 (36%) | 13/36 (36%) | 7/36 (19%) | 4/36 (11%) |
| 5 | 19/36 (53%) | 17/36 (47%) | 12/36 (33%) | 11/36 (31%) | 6/36 (17%) |
| 6 | 17/36 (47%) | 14/36 (39%) | 10/36 (28%) | 9/36 (25%) | 7/36 (19%) |

TABLE 9-continued

Predicted vs. Observed Linear regression Coefficients for Continuous Dependent Variables In Patients with Severe Sepsis From Serial Data

| Days After Baseline | Regression Coefficient | | | | |
|---|---|---|---|---|---|
| | >0.5 | >0.6 | >0.7 | >0.8 | >0.9 |
| 7 | 14/36 (39%) | 12/36 (33%) | 11/36 (31%) | 7/36 (19%) | 5/36 (14%) |
| 14 | 10/36 (28%) | 9/36 (25%) | 6/36 (17%) | 6/36 (17%) | 5/36 (14%) |
| 21 | 13/36 (36%) | 11/36 (31%) | 10/36 (28%) | 8/36 (22%) | 7/36 (19%) |
| 28 | 11/36 (31%) | 10/36 (28%) | 7/36 (19%) | 7/36 (19%) | 5/36 (14%) |

Example 10

Multiple Imputation Analysis Modeling Via SMART

Additional SMART profiles were generated from a database of patients with severe sepsis based only upon selected physiologic variables, selected standard hospital laboratory tests and selected patient demographics. Patients were randomly separated into two sets, one to be modeled (n=200) and one to validate the created models (n=102). Logistic regression was performed to predict the outcomes of organ failure, shock, ventilation and GCS. The independent variables were chosen by stepwise selection in each of five data sets to develop, at most, five different models to choose from. To determine which of the five possible models contained the best independent variables, each set of variables was modeled with the five data sets providing five different results. The deviance (−2 log likelihood) was averaged from the five different results to compare the models. The likelihood ratio test determined the best set of variables to create the best model.

The five results for the best mode were then averaged to summarize the hosmer-lemeshow test, and the area under the ARC curve. Also, the parameter estimates were averaged in accordance with the standard analysis of multiple imputation. The final models were validated by using the same patients set aside from each of the five complete data sets. The results of the area under the ARC curve were averaged to summarize the results. Results for an ARDS model, an HBD model, a shock model, an ARF model, a GSC model, a DIC model, and a VENT model are shown in the following Tables.

Table 10 provides a summary of the best models for each day a patient could have ARDS. As shown in the Table, there are five results for each day from each of the five imputed sets.

TABLE 10

ARDS Model Summary

Hosmer and Lemeshow

| Imputed Sets | chi-sq | p-values | roc | roc |
|---|---|---|---|---|
| DAY 1 (Variables used to generate profile include aado2 ards_xy peep rptvol ards0 intra_abdominal_pelvis) | | | | |
| 1 | 2.26 | 0.97 | 0.935 | 0.824 |
| 2 | 11.08 | 0.2 | 0.935 | 0.823 |
| 3 | 7.5 | 0.48 | 0.947 | 0.811 |
| 4 | 5.4 | 0.71 | 0.941 | 0.803 |
| 5 | 10.99 | 0.2 | 0.945 | 0.846 |
| Average | | 0.512 | 0.941 | 0.8214 |
| DAY 2 (Variables used to generate profile include bmi ards0 gasti_inf urinary_tract) | | | | |
| 1 | 1.79 | 0.99 | 0.949 | 0.816 |
| 2 | 3.56 | 0.89 | 0.951 | 0.823 |
| 3 | 5.22 | 0.73 | 0.944 | 0.819 |
| 4 | 3.99 | 0.86 | 0.949 | 0.821 |
| 5 | 3.43 | 0.9 | 0.947 | 0.83 |
| Average | | 0.874 | 0.948 | 0.8218 |
| DAY 3 (Variables used to generate profile include peep pe_heent ards0 gasti_inf) | | | | |
| 1 | 8.23 | 0.41 | 0.903 | 0.807 |
| 2 | 2.97 | 0.89 | 0.869 | 0.814 |
| 3 | 5.37 | 0.61 | 0.91 | 0.816 |
| 4 | 5.36 | 0.72 | 0.899 | 0.798 |
| 5 | 7.32 | 0.4 | 0.896 | 0.816 |
| Average | | 0.606 | 0.895 | 0.8096 |
| DAY 4 (Variables used to generate profile include albun bmi pe_heent ards0 arf0 gasti_inf lad pulse uflpvc) | | | | |
| 1 | 4.24 | 0.83 | 0.964 | 0.722 |
| 2 | 6.28 | 0.62 | 0.961 | 0.714 |
| 3 | 4.6 | 0.8 | 0.961 | 0.734 |
| 4 | 5.1 | 0.74 | 0.96 | 0.717 |
| 5 | 6.2 | 0.63 | 0.96 | 0.734 |
| Average | | 0.724 | 0.961 | 0.7242 |
| DAY 5 (Variables used to generate profile include albun endocrine_metabolic pe_heent ufin24 ards0 gasti_inf lad) | | | | |
| 1 | 6.1 | 0.64 | 0.946 | 0.717 |
| 2 | 7.8 | 0.45 | 0.945 | 0.706 |
| 3 | 3.5 | 0.9 | 0.947 | 0.712 |
| 4 | 2.4 | 0.97 | 0.941 | 0.7 |
| 5 | 13.1 | 0.11 | 0.939 | 0.718 |
| Average | | 0.614 | 0.944 | 0.7106 |
| DAY 6 (Variables used to generate profile include albun endocrine_metabolic pe_heent ards0 gasti_inf uflpvc) | | | | |
| 1 | 10.3 | 0.25 | 0.924 | 0.757 |
| 2 | 7.4 | 0.49 | 0.916 | 0.751 |
| 3 | 8.1 | 0.43 | 0.922 | 0.765 |
| 4 | 7.6 | 0.37 | 0.916 | 0.741 |
| 5 | 8.3 | 0.4 | 0.919 | 0.754 |
| Average | | 0.388 | 0.92 | 0.7536 |
| DAY 7 (Variables used to generate profile include curea endocrine_metabolic ufin24 ards0 gasti_inf lungcanc_xy) | | | | |
| 1 | 3.6 | 0.9 | 0.914 | 0.686 |
| 2 | 5.2 | 0.73 | 0.922 | 0.685 |
| 3 | 1.8 | 0.99 | 0.935 | 0.691 |

TABLE 10-continued

ARDS Model Summary

Hosmer and Lemeshow

| Imputed Sets | chi-sq | p-values | roc | roc |
|---|---|---|---|---|
| 4 | 4.8 | 0.78 | 0.916 | 0.674 |
| 5 | 3.1 | 0.93 | 0.949 | 0.69 |
| Average | | 0.866 | 0.927 | 0.6852 |

TABLE 11

HBD Model Summary

Hosmer and Lemeshow

| Imputed Sets | chi-sq | p-values | roc | roc |
|---|---|---|---|---|
| DAY 1 (Variables used to generate profile ctbil unknown hbd0) | | | | |
| 1 | 5.8 | 0.66 | 0.881 | 0.791 |
| 2 | 9.7 | 0.29 | 0.883 | 0.781 |
| 3 | 3.7 | 0.88 | 0.882 | 0.812 |
| 4 | 2 | 0.98 | 0.885 | 0.817 |
| 5 | 4.8 | 0.77 | 0.879 | 0.817 |
| Average | | 0.716 | 0.882 | 0.800 |
| DAY 2 (Variables used to generate profile include blood curea qt rptvol renal wbc hbd0) | | | | |
| 1 | 7.4 | 0.48 | 0.884 | 0.696 |
| 2 | 7.9 | 0.45 | 0.876 | 0.705 |
| 3 | 4.6 | 0.8 | 0.870 | 0.702 |
| 4 | 3 | 0.93 | 0.882 | 0.707 |
| 5 | 8.7 | 0.37 | 0.875 | 0.707 |
| Average | | 0.606 | 0.877 | 0.703 |
| DAY 3 (Variables used to generate profile include hwbc mchc pe_extremities_joints pe_heent pe_neurological hbd0 skin_wound) | | | | |
| 1 | 3.7 | 0.88 | 0.916 | 0.715 |
| 2 | 3.9 | 0.86 | 0.915 | 0.708 |
| 3 | 6.7 | 0.58 | 0.908 | 0.715 |
| 4 | 2.7 | 0.95 | 0.912 | 0.715 |
| 5 | 1.4 | 0.99 | 0.923 | 0.720 |
| Average | | 0.848 | 0.915 | 0.715 |
| DAY 4 (Variables used to generate profile include apco2 cardiovascular fio2 pe_skin_appearance unknown hbd0) | | | | |
| 1 | 15.7 | 0.05 | 0.854 | 0.715 |
| 2 | 16.3 | 0.04 | 0.855 | 0.717 |
| 3 | 16.4 | 0.04 | 0.854 | 0.714 |
| 4 | 16.5 | 0.04 | 0.855 | 0.710 |
| 5 | 18.2 | 0.02 | 0.855 | 0.715 |
| Average | | 0.038 | 0.855 | 0.714 |
| DAY 5 (Variables used to generate profile include pe_neurological hbd0) | | | | |
| 1 | 3.7 | 0.88 | 0.916 | 0.715 |
| 2 | 3.9 | 0.86 | 0.915 | 0.708 |
| 3 | 6.7 | 0.56 | 0.908 | 0.715 |
| 4 | 2.7 | 0.95 | 0.912 | 0.715 |
| 5 | 1.4 | 0.99 | 0.923 | 0.720 |
| Average | | 0.848 | 0.915 | 0.715 |
| DAY 6 (Variables used to generate profile include apco2 ctbil hbd0) | | | | |
| 1 | 0.003 | 0.99 | 0.767 | 0.768 |
| 2 | 0.003 | 0.99 | 0.767 | 0.722 |
| 3 | 0.03 | 0.99 | 0.767 | 0.768 |
| 4 | 0.003 | 0.99 | 0.767 | 0.768 |

TABLE 11-continued

HBD Model Summary

Hosmer and Lemeshow

| Imputed Sets | chi-sq | p-values | roc | roc |
|---|---|---|---|---|
| 5 | 0.003 | 0.99 | 0.767 | 0.753 |
| Average | | 0.99 | 0.767 | 0.756 |
| DAY 7 (Variables used to generate profile include apo2 asat bmi pe_heent pe_neurological pe_skin_appearance hbd0) | | | | |
| 1 | 10.7 | 0.24 | 0.848 | 0.650 |
| 2 | 5.3 | 0.72 | 0.883 | 0.665 |
| 3 | 3.8 | 0.87 | 0.869 | 0.547 |
| 4 | 8.8 | 0.36 | 0.851 | 0.649 |
| 5 | 5.7 | 0.68 | 0.880 | 0.653 |
| Average | | 0.574 | 0.866 | 0.653 |

TABLE 12

SHOCK Model Summary

Hosmer and Lemeshow

| Imputed Sets | chi-sq | p-values | roc | roc |
|---|---|---|---|---|
| DAY 1 (Variables used to generate profile include PE_Other_body_region vasco) | | | | |
| 1 | 0.55 | 0.45 | 0.710 | 0.665 |
| 2 | 0.57 | 0.45 | 0.710 | 0.665 |
| 3 | 0.57 | 0.45 | 0.710 | 0.665 |
| 4 | 0.57 | 0.45 | 0.710 | 0.665 |
| 5 | 0.57 | 0.45 | 0.710 | 0.665 |
| Average | | | | |
| DAY 2 (Variables used to generate profile include albun ctbil gsc1 hgb lahb map) | | | | |
| 1 | 7.3 | 0.51 | 0.734 | 0.609 |
| 2 | 7.1 | 0.52 | 0.751 | 0.613 |
| 3 | 7.5 | 0.49 | 0.759 | 0.628 |
| 4 | 7.4 | 0.49 | 0.752 | 0.607 |
| 5 | 10.9 | 0.21 | 0.764 | 0.632 |
| Average | | 0.444 | 0.752 | 0.617 |
| DAY 3 (Variables used to generate profile include vrate map) | | | | |
| 1 | 4.1 | 0.85 | 0.734 | 0.570 |
| 2 | 2.4 | 0.97 | 0.728 | 0.568 |
| 3 | 2.7 | 0.95 | 0.737 | 0.587 |
| 4 | 3.5 | 0.9 | 0.737 | 0.563 |
| 5 | 4.5 | 0.81 | 0.741 | 0.572 |
| Average | | 0.896 | 0.735 | 0.572 |
| DAY 4 (Variables used to generate profile include curea pe_abdomen uomlkh map xyabnormal) | | | | |
| 1 | 7.9 | 0.45 | 0.803 | 0.606 |
| 2 | 7.4 | 0.31 | 0.796 | 0.606 |
| 3 | 8.9 | 0.35 | 0.794 | 0.576 |
| 4 | 4.3 | 0.83 | 0.806 | 0.614 |
| 5 | 5.2 | 0.74 | 0.793 | 0.594 |
| Average | | 0.536 | 0.798 | 0.599 |
| DAY 5 (Variables used to generate profile include alveolar mcv oldmi albun) | | | | |
| 1 | 11.7 | 0.18 | 0.740 | 0.669 |
| 2 | 10.4 | 0.24 | 0.764 | 0.708 |
| 3 | 5.4 | 0.91 | 0.777 | 0.697 |
| 4 | 15.2 | 0.06 | 0.790 | 0.671 |
| 5 | 3.5 | 0.9 | 0.748 | 0.691 |
| Average | | 0.454 | 0.764 | 0.687 |
| DAY 6 (Variables used to generate profile include wbc respt_inf) | | | | |
| 1 | 6.1 | 0.64 | 0.653 | 0.544 |
| 2 | 7.7 | 0.36 | 0.660 | 0.552 |

TABLE 12-continued

SHOCK Model Summary

| | Hosmer and Lemeshow | | | |
|---|---|---|---|---|
| Imputed Sets | chi-sq | p-values | roc | roc |
| 3 | 5.3 | 0.63 | 0.649 | 0.565 |
| 4 | 7.2 | 0.41 | 0.643 | 0.552 |
| 5 | 6.9 | 0.55 | 0.663 | 0.549 |
| Average | | 0.518 | 0.654 | 0.552 |
| DAY 7 (Variables used to generate profile include albun alveolar cirrhosis_mf_inf curea gsc1 hwbc rtrr foreign_body_cat) | | | | |
| 1 | 0.63 | 0.9 | 0.626 | 0.617 |
| 2 | 0.38 | 0.94 | 0.615 | 0.615 |
| 3 | 0.73 | 0.67 | 0.625 | 0.613 |
| 4 | 0.42 | 0.93 | 0.620 | 0.611 |
| 5 | 0.66 | 0.88 | 0.620 | 0.617 |
| Average | | 0.904 | 0.621 | 0.615 |

TABLE 13

ARF Model Summary

| | Hosmer and Lemeshow | | | |
|---|---|---|---|---|
| Imputed Sets | chi-sq | p-values | roc | roc |
| DAY 1 (Variables used to generate profile include apao2 icu_inf arf0 mvent) | | | | |
| 1 | 0.957 | 0.8 | 0.957 | 0.776 |
| 2 | 0.959 | 0.82 | 0.959 | 0.776 |
| 3 | 0.957 | 0.81 | 0.957 | 0.774 |
| 4 | 0.959 | 0.81 | 0.959 | 0.773 |
| 5 | 0.958 | 0.78 | 0.958 | 0.776 |
| Average | | 0.804 | 0.958 | 0.775 |
| DAY 2 (Variables used to generate profile include ccreat hepatic_biliary pr arf0 diffuse_xy intra_abdominal_pelvis) | | | | |
| 1 | 9.8 | 0.28 | 0.943 | 0.842 |
| 2 | 9.5 | 0.3 | 0.943 | 0.828 |
| 3 | 10.1 | 0.26 | 0.944 | 0.831 |
| 4 | 11.3 | 0.19 | 0.944 | 0.836 |
| 5 | 12.1 | 0.15 | 0.944 | 0.828 |
| Average | | 0.236 | 0.944 | 0.833 |
| DAY 3 (Variables used to generate profile include fio2 hepatic_biliary pr rstrol art0 dic0 resp respt_inf tracing) | | | | |
| 1 | 0.69 | 0.99 | 0.975 | 0.887 |
| 2 | 4 | 0.78 | 0.966 | 0.890 |
| 3 | 2.5 | 0.96 | 0.965 | 0.882 |
| 4 | 3.6 | 0.89 | 0.965 | 0.884 |
| 5 | 2.7 | 0.95 | 0.962 | 0.888 |
| Average | | 0.914 | 0.967 | 0.882 |
| DAY 4 (Variables used to generate profile include hepatic_biliary arf0 dic0 tracing) | | | | |
| 1 | 1.7 | 0.8 | 0.880 | 0.843 |
| 2 | 1.7 | 0.8 | 0.880 | 0.843 |
| 3 | 1.7 | 0.8 | 0.880 | 0.843 |
| 4 | 1.7 | 0.8 | 0.880 | 0.843 |
| 5 | 1.7 | 0.8 | 0.880 | 0.843 |
| Average | | 0.8 | 0.880 | 0.843 |
| DAY 5 (Variables used to generate profile include hepatic_biliary pneum_xy arf0 foreign_body_catheter) | | | | |
| 1 | 2.9 | 0.71 | 0.888 | 0.818 |
| 2 | 2.9 | 0.72 | 0.888 | 0.826 |
| 3 | 2.9 | 0.71 | 0.888 | 0.826 |
| 4 | 2.9 | 0.71 | 0.888 | 0.824 |

TABLE 13-continued

ARF Model Summary

| | Hosmer and Lemeshow | | | |
|---|---|---|---|---|
| Imputed Sets | chi-sq | p-values | roc | roc |
| 5 | 2.9 | 0.74 | 0.888 | 0.820 |
| Average | | 0.718 | 0.888 | 0.823 |
| DAY 6 (Variables used to generate profile include arf0 diffuse_xy) | | | | |
| 1 | 0.89 | 0.96 | 0.862 | 0.738 |
| 2 | 0.09 | 0.96 | 0.862 | 0.738 |
| 3 | 0.11 | 0.95 | 0.863 | 0.738 |
| 4 | 0.09 | 0.96 | 0.862 | 0.738 |
| 5 | 0.11 | 0.95 | 0.863 | 0.738 |
| Average | | 0.956 | 0.862 | 0.738 |
| DAY 7 | | | | |
| 1 | 4.4 | 0.49 | 0.886 | 0.739 |
| 2 | 3.4 | 0.49 | 0.886 | 0.739 |
| 3 | 3.4 | 0.49 | 0.886 | 0.739 |
| 4 | 3.4 | 0.49 | 0.886 | 0.739 |
| 5 | 3.4 | 0.49 | 0.886 | 0.739 |
| Average | | 0.49 | 0.886 | 0.739 |

TABLE 14

GSC Model Summary

| | Hosmer and Lemeshow | | | |
|---|---|---|---|---|
| Imputed Sets | chi-sq | p-values | roc | roc |
| DAY 3 (Variables used to generate profile include csod gsc1 pedema_xy) | | | | |
| 1 | 0.97 | 0.280 | 0.860 | 0.710 |
| 2 | 806 | 0.360 | 0.907 | 0.692 |
| 3 | 12.8 | 0.120 | 0.917 | 0.734 |
| 4 | 33.1 | 0.000 | 0.874 | 0.727 |
| 5 | 14 | 0.080 | 0.869 | 0.700 |
| Average | | 0.168 | 0.885 | 0.713 |
| DAY 4 (Variables used to generate profile include abd gsc1 pt) | | | | |
| 1 | 10.8 | 0.210 | 0.878 | 0.727 |
| 2 | 10 | 0.860 | 0.881 | 0.742 |
| 3 | 6.5 | 0.590 | 0.923 | 0.694 |
| 4 | 24 | 0.002 | 0.887 | 0.699 |
| 5 | 13 | 0.130 | 0.891 | 0.719 |
| Average | | 0.358 | 0.692 | 0.716 |
| DAY 5 (Variables used to generate profile include fio2 gsc1 weight dic0 oldmi) | | | | |
| 1 | 6.5 | 0.600 | 0.883 | 0.650 |
| 2 | 11 | 0.200 | 0.892 | 0.650 |
| 3 | 6.1 | 0.630 | 0.818 | 0.714 |
| 4 | 5.7 | 0.680 | 0.883 | 0.640 |
| 5 | 5 | 0.750 | 0.893 | 0.684 |
| Average | | 0.572 | 0.874 | 0.668 |
| DAY 7 (Variables used to generate profile include dic0) | | | | |
| 1 | NEI | NEI | 0.644 | 0.718 |
| 2 | | | 0.644 | 0.718 |
| 3 | | | 0.644 | 0.718 |
| 4 | | | 0.644 | 0.718 |
| 5 | | | 0.644 | 0.718 |
| Average | | | 0.644 | 0.718 |

NEI = Not enough information to general results

TABLE 15

DIC Model Summary

| Imputed Sets | Hosmer and Lemeshow chi-sq | p-values | roc | roc |
|---|---|---|---|---|
| DAY 1 (Variables used to generate profile include fio2 dic0 1bbb mfmpvc rvh temp) | | | | |
| 1 | 5.9 | 0.66 | 0.907 | 0.748 |
| 2 | 3.1 | 0.92 | 0.907 | 0.748 |
| 3 | 3.1 | 0.93 | 0.907 | 0.748 |
| 4 | 3.1 | 0.93 | 0.907 | 0.748 |
| 5 | 3.1 | 0.93 | 0.907 | 0.748 |
| Average | | 8.74 | 0.907 | 0.748 |
| DAY 2 (Variables used to generate profile include fio2 hgb qt utotml dic0 temp) | | | | |
| 1 | 4.9 | 0.77 | 0.889 | 0.896 |
| 2 | 8.1 | 0.42 | 0.866 | 0.865 |
| 3 | 6 | 0.65 | 0.888 | 0.881 |
| 4 | 7.23 | 0.51 | 0.898 | 0.761 |
| 5 | 4.2 | 0.84 | 0.892 | 0.892 |
| Average | | 0.638 | 0.887 | 0.855 |
| DAY 3 (Variables used to generate profile include csod curea fio2 dic0 rad wnd_inf) | | | | |
| 1 | 6.2 | 0.62 | 0.865 | 0.657 |
| 2 | 8.4 | 0.39 | 0.864 | 0.667 |
| 3 | 6.2 | 0.62 | 0.086 | 0.657 |
| 4 | 6.2 | 0.62 | 0.865 | 0.657 |
| 5 | 8.4 | 0.39 | 0.865 | 0.657 |
| Average | | 0.528 | 0.709 | 0.657 |
| DAY 4 (Variables used to generate profile include fio2 renal uomlkh dic0) | | | | |
| 1 | 13.2 | 0.1 | 0.887 | 0.521 |
| 2 | 9.1 | 0.33 | 0.892 | 0.543 |
| 3 | 2.6 | 0.96 | 0.885 | 0.546 |
| 4 | 2.3 | 0.97 | 0.885 | 0.585 |
| 5 | 8.5 | 0.38 | 0.883 | 0.603 |
| Average | | 0.548 | 0.886 | 0.560 |
| DAY 5 (Variables used to generate profile include renal afio (only 6 had dic)) | | | | |
| 1 | 0.27 | 0.6 | 0.839 | 0.413 |
| 2 | 0.27 | 0.6 | 0.839 | 0.413 |
| 3 | 0.27 | 0.6 | 0.839 | 0.413 |
| 4 | 0.27 | 0.6 | 0.839 | 0.413 |
| 5 | 0.27 | 0.6 | 0.839 | 0.413 |
| Average | | 0.6 | 0.839 | 0.413 |
| DAY 6 (Variables used to generate profile include dic0 pulse temp height renal blood) | | | | |
| 1 | 9.4 | 0.31 | 0.854 | 0.642 |
| 2 | 12.7 | 0.12 | 0.853 | 0.622 |
| 3 | 19.9 | 0.01 | 0.859 | 0.627 |
| 4 | 3.7 | 0.89 | 0.890 | 0.669 |
| 5 | 21.8 | 0.005 | 0.855 | 0.619 |
| Average | | 0.267 | 0.862 | 0.636 |
| DAY 7 (Variables used to generate profile include dic0 uomikh wbc) | | | | |
| 1 | 1.6 | 0.98 | 0.950 | 0.773 |
| 2 | 0.7 | 0.99 | 0.966 | 0.767 |
| 3 | 1.7 | 0.99 | 0.950 | 0.793 |
| 4 | 2.1 | 0.98 | 0.958 | 0.806 |
| 5 | 2.1 | 0.98 | 0.966 | 0.790 |
| Average | | 0.984 | 0.958 | 0.786 |

TABLE 16

VENT Model Summary

| Imputed Sets | Hosmer and Lemeshow chi-sq | p-values | roc | roc |
|---|---|---|---|---|
| DAY 1 (Variables used to generate profile include ccreat hbd0 mvent) | | | | |
| 1 | 5.4 | 0.72 | 0.967 | 0.809 |
| 2 | 5.4 | 0.72 | 0.967 | 0.809 |
| 3 | 5.4 | 0.72 | 0.967 | 0.809 |
| 4 | 5.4 | 0.72 | 0.967 | 0.809 |
| 5 | 5.4 | 0.72 | 0.967 | 0.809 |
| Average | | 0.72 | 0.967 | 0.809 |
| DAY 2 (Variables used to generate profile include abd arf0 emphysema hbd0 mvent pulse) | | | | |
| 1 | 5.4 | 0.72 | 0.871 | 0.790 |
| 2 | 7.2 | 0.51 | 0.865 | 0.766 |
| 3 | 5.4 | 0.71 | 0.858 | 0.799 |
| 4 | 3.7 | 0.88 | 0.874 | 0.764 |
| 5 | 9.2 | 0.34 | 0.872 | 0.809 |
| Average | | 0.632 | 0.868 | 0.786 |
| DAY 3 (Variables used to generate profile include apco2 apo2 asat hbd0 mvent) | | | | |
| 1 | 4.8 | 0.77 | 0.835 | 0.800 |
| 2 | 7.4 | 0.49 | 0.852 | 0.804 |
| 3 | 10.8 | 0.21 | 0.852 | 0.782 |
| 4 | 8.7 | 0.37 | 0.851 | 0.791 |
| 5 | 5.4 | 0.71 | 0.844 | 0.790 |
| Average | | 0.51 | 0.847 | 0.793 |
| DAY 4 (Variables used to generate profile include apo2 curea hbd0 mvent) | | | | |
| 1 | 7.5 | 0.84 | 0.807 | 0.702 |
| 2 | 7.5 | 0.84 | 0.807 | 0.705 |
| 3 | 7.5 | 0.84 | 0.807 | 0.705 |
| 4 | 7.5 | 0.84 | 0.807 | 0.705 |
| 5 | 7.5 | 0.84 | 0.807 | 0.706 |
| Average | | 0.84 | 0.807 | 0.705 |
| DAY 5 (Variables used to generate profile include gsc1 respiratory ards0 gast_inf mvent resp) | | | | |
| 1 | 28.4 | 0.0004 | 0.833 | 0.770 |
| 2 | 21.8 | 0.005 | 0.840 | 0.771 |
| 3 | 18.7 | 0.02 | 0.832 | 0.778 |
| 4 | 25 | 0.0002 | 0.837 | 0.757 |
| 5 | 13.5 | 0.09 | 0.852 | 0.764 |
| Average | | 0.02348 | 0.839 | 0.768 |
| DAY 6 (Variables used to generate profile include gsc1 hepatic_biliary peep bpdia mvent pulse) | | | | |
| 1 | 3 | 0.93 | 0.816 | 0.723 |
| 2 | 6.6 | 0.58 | 0.812 | 0.701 |
| 3 | 9.2 | 0.32 | 0.841 | 0.724 |
| 4 | 7.3 | 0.51 | 0.832 | 0.699 |
| 5 | 4.4 | 0.82 | 0.822 | 0.733 |
| Average | | 0.632 | 0.825 | 0.716 |
| DAY 7 (Variables used to generate profile include rtrr ards0 respt_inf) | | | | |
| 1 | 3.3 | 0.86 | 0.778 | 0.495 |
| 2 | 6.9 | 0.44 | 0.780 | 0.495 |
| 3 | 6 | 0.64 | 0.789 | 0.495 |
| 4 | 5.7 | 0.57 | 0.784 | 0.481 |
| 5 | 6.3 | 0.5 | 0.722 | 0.496 |
| Average | | 0.602 | 0.771 | 0.492 |

TABLE 17

DIC Model Summary

Hosmer and Lemeshow

| Imputed Sets | chi-sq | p-values | roc | roc |
|---|---|---|---|---|
| DAY 1 (Variables used to generate profile include fio2 dic0 lbbb mfmpvc rvh temp) | | | | |
| 1 | 5.9 | 0.66 | 0.907 | 0.748 |
| 2 | 3.1 | 0.92 | 0.907 | 0.748 |
| 3 | 3.1 | 0.93 | 0.907 | 0.748 |
| 4 | 3.1 | 0.93 | 0.907 | 0.748 |
| 5 | 3.1 | 0.93 | 0.907 | 0.748 |
| Average | | 0.874 | 0.907 | 0.748 |
| DAY 2 (Variables used to generate profile include fio2 hgb qt utotml dic0 temp) | | | | |
| 1 | 4.9 | 0.77 | 0.889 | 0.896 |
| 2 | 8.1 | 0.42 | 0.866 | 0.865 |
| 3 | 6 | 0.65 | 0.888 | 0.861 |
| 4 | 7.23 | 0.51 | 0.898 | 0.751 |
| 5 | 4.2 | 0.84 | 0.892 | 0.892 |
| Average | | 0.638 | 0.887 | 0.855 |
| DAY 3 (Variables used to generate profile include csod curea fio2 dic0 rad wnd_inf) | | | | |
| 1 | 6.2 | 0.62 | 0.865 | 0.657 |
| 2 | 8.4 | 0.39 | 0.864 | 0.657 |
| 3 | 6.2 | 0.62 | 0.086 | 0.657 |
| 4 | 6.2 | 0.62 | 0.865 | 0.657 |
| 5 | 8.4 | 0.39 | 0.865 | 0.657 |
| Average | | 0.528 | 0.709 | 0.657 |
| DAY 4 (Variables used to generate profile include fio2 renal uomlkh dic0) | | | | |
| 1 | 13.2 | 0.1 | 0.887 | 0.521 |
| 2 | 9.1 | 0.33 | 0.892 | 0.543 |
| 3 | 2.6 | 0.96 | 0.885 | 0.546 |
| 4 | 2.3 | 0.97 | 0.885 | 0.585 |
| 5 | 8.5 | 0.38 | 0.883 | 0.603 |
| Average | | 0.548 | 0.886 | 0.560 |
| DAY 5 (Variables used to generate profile include renal afib (only 6 had dic)) | | | | |
| 1 | 0.27 | 0.6 | 0.839 | 0.413 |
| 2 | 0.27 | 0.6 | 0.839 | 0.413 |
| 3 | 0.27 | 0.6 | 0.839 | 0.413 |
| 4 | 0.27 | 0.6 | 0.839 | 0.413 |
| 5 | 0.27 | 0.6 | 0.839 | 0.413 |
| Average | | 0.6 | 0.839 | 0.413 |
| DAY 6 (Variables used to generate profile include dic0 pulse temp height renal blood) | | | | |
| 1 | 9.4 | 0.31 | 0.854 | 0.642 |
| 2 | 12.7 | 0.12 | 0.853 | 0.622 |
| 3 | 19.9 | 0.01 | 0.859 | 0.627 |
| 4 | 3.7 | 0.89 | 0.890 | 0.669 |
| 5 | 21.8 | 0.005 | 0.855 | 0.619 |
| Average | | 0.267 | 0.862 | 0.636 |
| DAY 7 (Variables used to generate profile include dic0 uomlkh wbc) | | | | |
| 1 | 1.6 | 0.98 | 0.950 | 0.773 |
| 2 | 0.7 | 0.99 | 0.966 | 0.767 |
| 3 | 1.7 | 0.99 | 0.950 | 0.793 |
| 4 | 2.1 | 0.98 | 0.958 | 0.806 |
| 5 | 2.1 | 0.98 | 0.966 | 0.790 |
| Average | | 0.984 | 0.958 | 0.786 |

Example 11

$E_5$ Anti-Endotoxin Antibody Responsiveness Identified Via SMART

Independent baseline, pre-randomized variables in the final SMART profile that identified patients who were appropriate biologically for E5 are provided in Table 18. Demographic analysis and clinical observations among the 759 consensus definition patients and the 388 SMART subjects are provided in Table 19. Differences in sex and race were not significant.

TABLE 18

Independent variables

| Variable | Odds Ratio Estimates | 95% Wald Confidence Limits |
|---|---|---|
| Apache II | 1.039 | 1.144 |
| Urinary Tract Source of Infection | 0.222 | 0.727 |
| Lung Source of Infection | 0.920 | 4.889 |
| Respiratory Rate | 1.008 | 1.071 |
| Diastolic Blood Pressure | 0.951 | 0.987 |
| DIC | 1.344 | 16.808 |
| Age | 1.027 | 1.067 |
| Neurologic Co-Morbidity | 1.344 | 5.185 |
| Acute Central Nervous Sys Dysfunction | 1.027 | 0.517 |
| ARDS | 3.702 | 18.304 |
| Hepatobiliary Dysfunction | 1.734 | 19.037 |

TABLE 19

Demographic and Clinical Observations

| | Consensus Criteria | | SMART Cohort | |
|---|---|---|---|---|
| | Placebo | E5 | Placebo | E5 |
| Sex: Men | 54% | 54% | 57% | 60% |
| Women | 46% | 43% | 40% | 40% |
| Race: Native American | 1.3% | 1.3% | 2.0% | 1.5% |
| Asian | 1.0% | 0.7% | 54% | 0.05% |
| African American | 24% | 24% | 28% | 25% |
| Caucasian | 70% | 69% | 63% | 66% |
| Hispanic | 5.7% | 4.9% | 5.8% | 6.5% |
| Other | 0.8% | 0.6% | 0.5% | 0.5% |
| Baseline Organ Failure | | | | |
| ARDS | 11% | 12% | 1.1% | 3.0% |
| Renal | 13.5% | 12% | 8.0% | 9.0% |
| CNS | 44% | 41% | 47% | 38% |
| DIC | 10.6% | 7.7% | 2.7% | 1.5% |
| Hepatobility | 7.6% | 4.4% | 54% | 0.5% |
| Shock | 1.6% | 1.0% | 0 | 0.5% |
| Gram Negative Infection | 35% | 35% | 41% | 42% |

What is claimed is:

1. A method for identifying a patient who meets clinical entry criteria of a study for a new therapeutic agent for treating sepsis and would respond favorably to the new therapeutic agent said method comprising:
   a) measuring physiological, respiratory, metabolic, renal, liver, hematologic and coagulation parameters of patients in clinical trials for a new therapeutic agent for treating sepsis;
   b) establishing a systemic mediator-associated response control profile from results of clinical trials in sepsis that identifies patients among whom the new therapeutic agent for sepsis has been shown to have demonstrated efficacy, wherein the control profile comprises one or more of the parameters in step a);
   c) measuring physiological, respiratory, metabolic, renal, liver, hematologic and coagulation parameters of a patient with sepsis;

d) generating a systemic mediator-associated response test profile for the patient with sepsis, said test profile comprising one or more of the parameters in step c); and e) comparing the parameters of the test profile with the same parameters of the control profile, wherein similarities in the parameters of the test profile and the parameters of the established control profile is indicative of a patient that would respond favorably in a clinical trial to the new therapeutic agent for sepsis.

* * * * *